(12) United States Patent
Dutta

(10) Patent No.: US 9,458,124 B2
(45) Date of Patent: Oct. 4, 2016

(54) SUBSTITUTED PYRAN DERIVATIVES

(71) Applicant: Wayne State University, Detroit, MI (US)

(72) Inventor: Aloke K. Dutta, Troy, MI (US)

(73) Assignee: Wayne State University, Detroit, MI (US)

(*) Notice: Subject to any disclaimer, the term of this patent is extended or adjusted under 35 U.S.C. 154(b) by 0 days.

(21) Appl. No.: 14/173,997

(22) Filed: Feb. 6, 2014

(65) Prior Publication Data

US 2014/0309427 A1   Oct. 16, 2014

Related U.S. Application Data

(60) Provisional application No. 61/761,310, filed on Feb. 6, 2013.

(51) Int. Cl.
| | | |
|---|---|---|
| *C07D 407/00* | (2006.01) | |
| *C07D 315/00* | (2006.01) | |
| *C07D 309/14* | (2006.01) | |
| *C07D 407/12* | (2006.01) | |
| *C07D 413/12* | (2006.01) | |
| *C07D 405/12* | (2006.01) | |
| *C07D 417/12* | (2006.01) | |

(52) U.S. Cl.
CPC ........... *C07D 309/14* (2013.01); *C07D 405/12* (2013.01); *C07D 407/12* (2013.01); *C07D 413/12* (2013.01); *C07D 417/12* (2013.01)

(58) Field of Classification Search
CPC .................................................. C07D 309/14
USPC ................................................... 549/414, 419
See application file for complete search history.

(56) References Cited

U.S. PATENT DOCUMENTS

| | | | | |
|---|---|---|---|---|
| 7,915,433 | B2* | 3/2011 | Dutta | 549/419 |
| 8,017,791 | B2* | 9/2011 | Dutta | 548/566 |
| 8,519,159 | B2* | 8/2013 | Dutta | C07D 309/10 |
| | | | | 548/465 |
| 8,841,464 | B2* | 9/2014 | Dutta | C07D 309/10 |
| | | | | 548/468 |
| 8,937,189 | B2* | 1/2015 | Dutta | 549/60 |

OTHER PUBLICATIONS

Zhang et al. Bioorganic & Medicinal Chemistry (2004), 12(23), 6301-6315.*
MacDougall, Journal of Molecular Graphics & Modelling (2008), 26(7), 1113-1124.*
Venkatesh et al., J. Pharm. Sci. 89, 145-54 (2000).*
Santra et al. ChemMedChem (2012), 7(12), 2093-2100.*

* cited by examiner

*Primary Examiner* — Nizal Chandrakumar
(74) *Attorney, Agent, or Firm* — Brooks Kushman P.C.

(57) ABSTRACT

Certain 3,6-disubstituted and 2,4,5-trisubstituted pyran derivatives that exhibit potent activity on monoamine transport systems are provided. The 3,6 and 2,4,5 pyrans are useful in probing the effects of their binding to monoamine transporter systems and the corresponding relationships to various afflictions affecting the CNS, or as a treatment for various CNS-related disorders in which the monoamine transport and related systems are implicated.

4 Claims, 12 Drawing Sheets

Figure 1A:
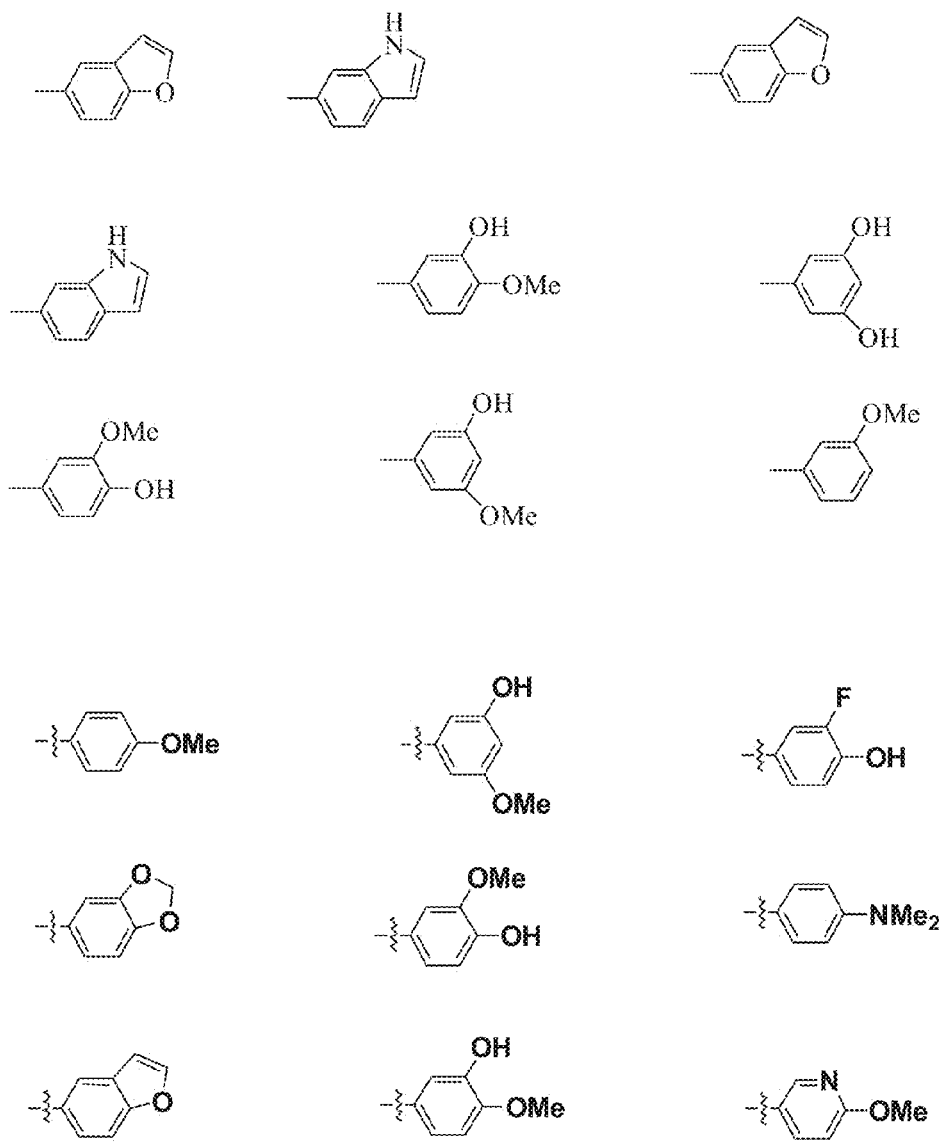

Scheme 4: Reagents and conditions: a) RCHO, 1,2-dichloroethane, MeOH, AcOH, NaCNBH$_3$ or Na(OAc)$_3$BH, rt. b) Anhyd. CH$_2$Cl$_2$, TFA, rt, 2 h.

Scheme 5: Reagents and conditions: a) Anhyd. CH$_2$Cl$_2$, −10 °C, Py., Tf$_2$O, 2 h. b) H$_2$O, 90 °C, 72 h. c) MeOH, Pd/C, H$_2$, rt, 1 atm, overnight. d) RCHO, 1,2-dichloroethane, MeOH, AcOH, NaCNBH$_3$ or Na(OAc)$_3$BH, rt.

SUBSTITUTED PYRAN DERIVATIVES

CROSS-REFERENCE TO RELATED APPLICATION

This application claims the benefit of U.S. provisional application Ser. No. 61/761,310, filed Feb. 6, 2013, the entire disclosure of which is hereby incorporated by reference.

STATEMENT REGARDING FEDERALLY SPONSORED RESEARCH OR DEVELOPMENT

The invention was made with Government support under Contract No. RO1 MH084888 awarded by the National Institutes of Health. The Government has certain rights to the invention.

BACKGROUND OF THE INVENTION

1. Field of the Invention

The invention pertains to pharmacologically active 3,6-disubstituted pyran compounds and similar compounds having additional substitution on the pyran ring. The compounds show high activity at monoamine transporters, and thus can be used to alter reuptake of monoamines in treatment of numerous diseases in mammalian species for which alteration of the monoamine transport system is indicated.

2. Background Art

The monoamine transporters terminate the action of released biogenic amines such as dopamine (DA), norepinephrine (NE) and serotonin (5-HT) in the central nervous system (CNS) and are known as dopamine transporter (DAT), norepinephrine transporter (NET) and serotonin transporter (SERT), respectively. These transporters play a vital role in maintaining the extracellular concentration of biogenic amine neurotransmitters. Drugs binding to the DAT are typically regarded as stimulants. Cocaine- and amphetamine-related compounds are known to produce their action by binding to both DAT and SERT with cocaine acting as a blocker and amphetamine as a substrate. On the other hand, drugs binding to the SERT and NET are known to produce, among other effects, potent antidepressant activity.

Major depression disorder is a significant health problem, and behind cardiovascular disease, depression is considered as the second most debilitating disease in the world. Unipolar depression is ranked number 1 before all other somatic and psychiatric illness. It is believed that more than 20% of individuals suffer from a depressive episode at least once in their lifetime. Depression is potentially fatal since many people suffering from depression contemplate suicide and other life threatening acts.

Selective monoamine uptake inhibitors have been implicated in the treatment of depression. In these classes specifically, serotonin and norepinephrine transporter blockers have been used in therapy for depression. Antidepressants are thought to elicit their therapeutic effects by increasing synaptic concentrations of serotonin and norepinephrine in the synapse.[14] Earlier developed tricyclic antidepressants acted by enhancing both serotonin and norepinephrine transmissions.[15] However, due to their non-specific interactions with the other CNS receptors, they exhibited toxic side effects which have limited their clinical use. Development of selective serotonin reuptake inhibitors (SSRI) alleviated many side effects exhibited by traditional tryciclic antidepressants and thus have proven to be more effective. However, the delayed onset action of SSRI sometime proved to have fatal consequences for patients afflicted with manic depression and in need of immediate help. SSRIs also have been implicated in number of other side effects which include insomnia, sexual dysfunction and nausea, etc. More recently, SSRIs have been implicated in suicide risk in adolescent population who were medicated with these drugs, raising some serious questions on the safety of SSRI. Lately, serotonin and norepinephrine dual uptake inhibitors have proven to be more efficacious in that regard. Fast onset of action associated with serotonin norepinephrine reuptake inhibitors (SNRI) was found to be more desirable as there is a pressing need for more faster acting antidepressant agents with reduced undesirable side effects.

SUMMARY

Against this prior art background, compound having formula I is provided:

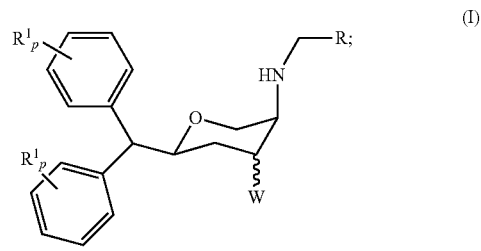

or a pharmaceutically acceptable derivative or salt thereof; wherein;
p is 0 to 5;
R is

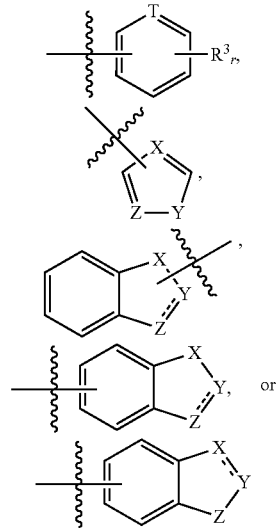

W is H, OH, or NHR°;
R° is H or $C_{1-18}$ alkyl;
R¹ is $C_{1-4}$ alkyl, $C_{2-6}$ alkenyl, $C_{2-6}$ optionally halogenated alkynyl, $C_{2-6}$ hydroxyalkynyl, halo, —CN, —COOR², $C_{5-10}$ cycloalkyl, $C_{2-18}$ alkenyl, —OH, —NO$_2$, —NHR², or —OR²;
R² is $C_{1-8}$ alkyl, $C_{5-6}$ cycloalkyl, or $C_{2-8}$ alkenyl;
R³ is F, Cl, Br, OR⁴, NO$_2$, NHR⁴, NH(CO)R⁴, N(CO)OR⁴, SO$_2$NH$_2$, or N(R⁴)$_2$; the dashed line is an optional bond;

T is CH or N;
r is 0 to 5;
X, Y, and Z are each independently $CR^4$, $CR^4_2$, C—$NHR^4$, C=O, S, N, or $NR^4$; and
$R^4$ is H or $C_{1-8}$ alkyl. The compounds of the present embodiment exhibit potent activity on monoamine transport systems, and are thus useful in probing the effects of binding to monoamine transport systems and the corresponding relationships to various afflictions affecting the CNS, or as a treatment for various CNS-related disorders in which the monoamine transport system is implicated. Moreover, these compounds operate as powerful blockers for monoamine transporters.

DETAILED DESCRIPTION OF THE DRAWINGS

Figure 1B:
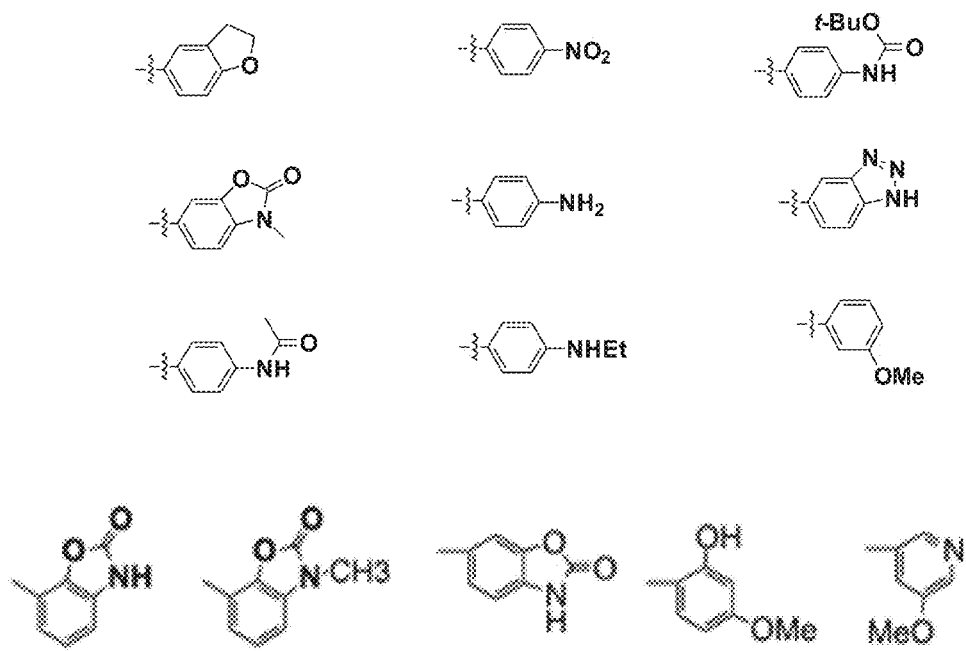
Figure 2:
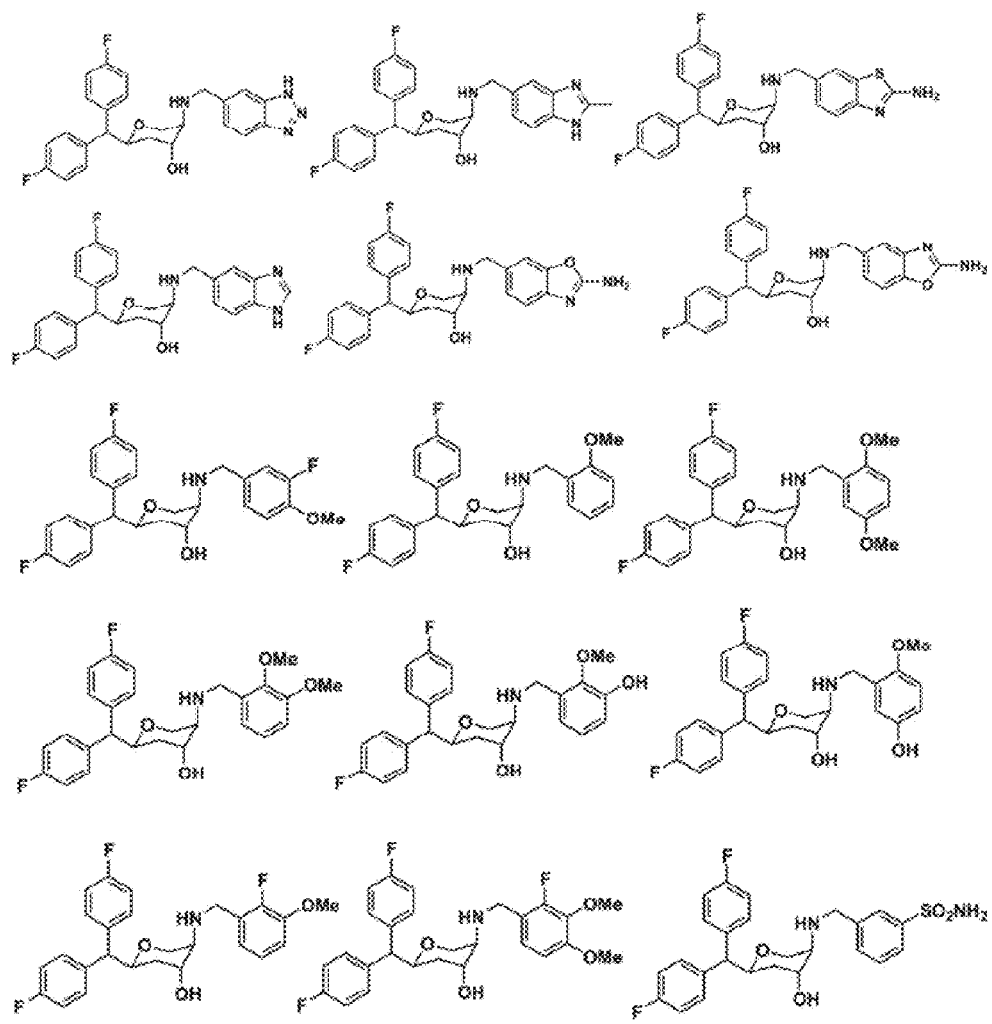
Figure 3:
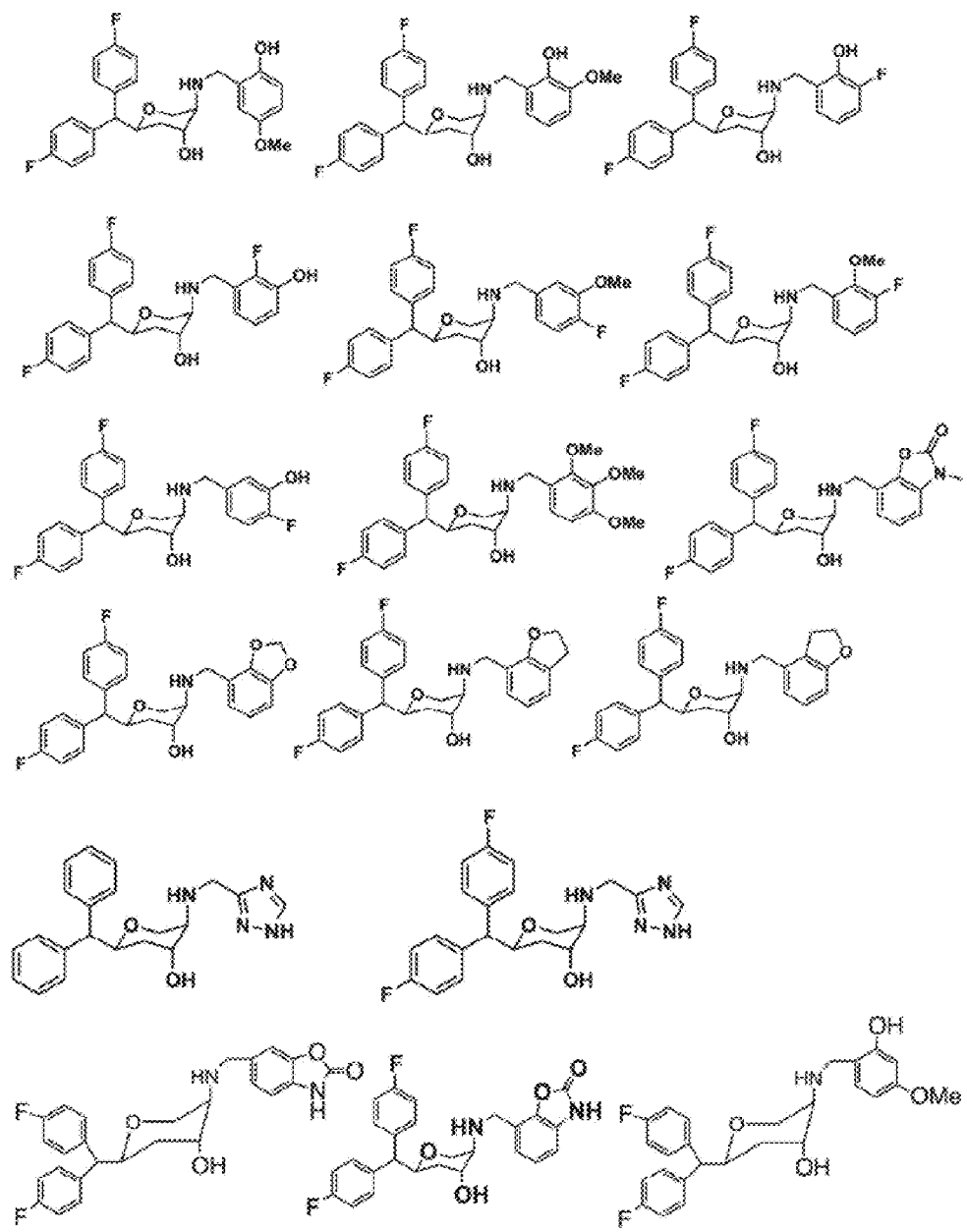
Figure 4:
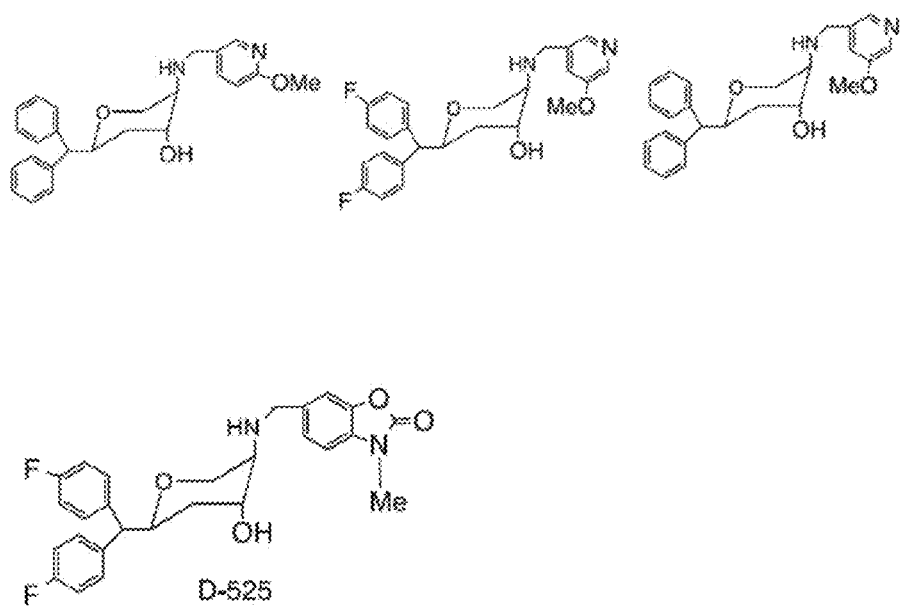
Figure 5:
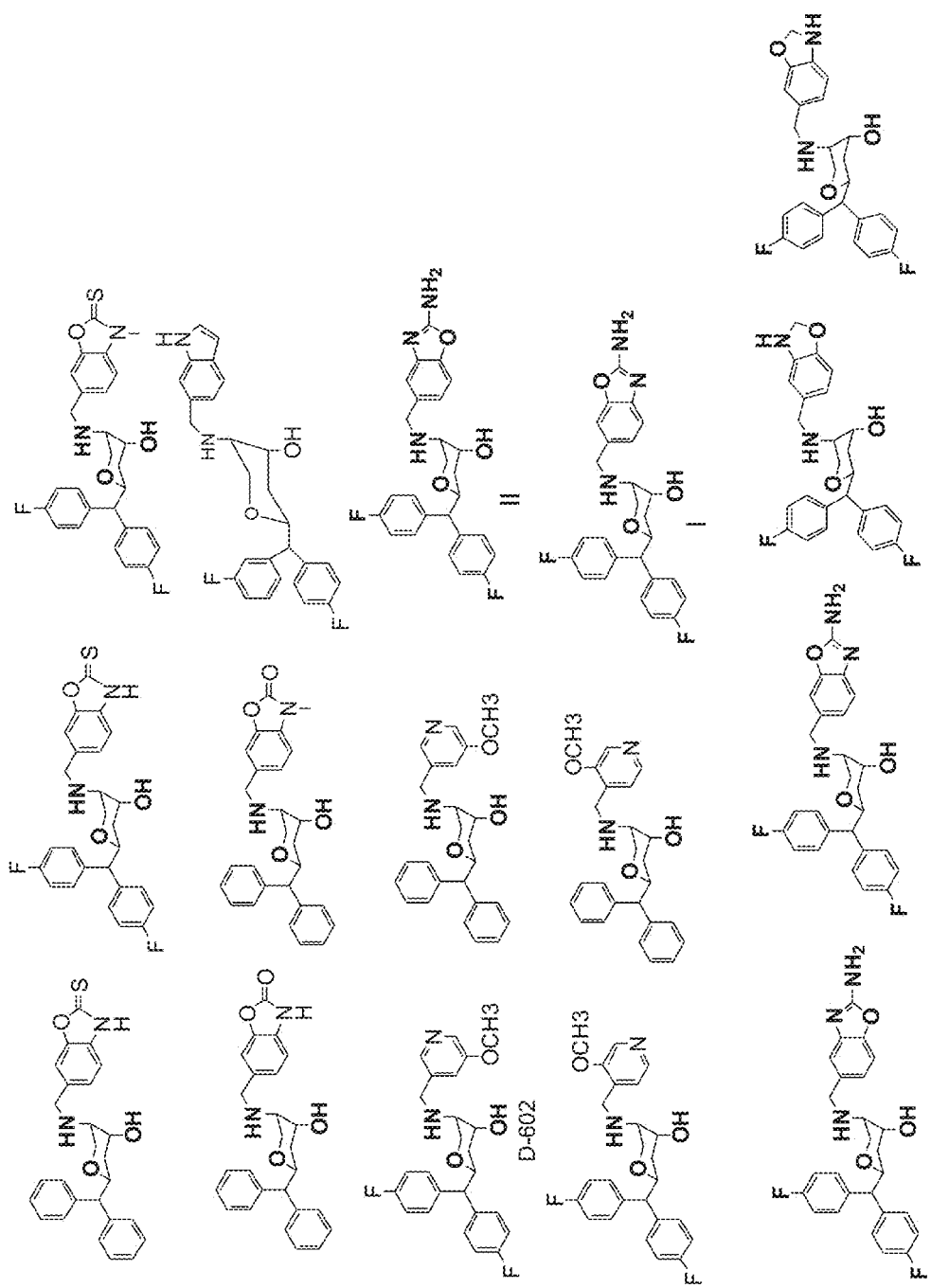
Figure 6:
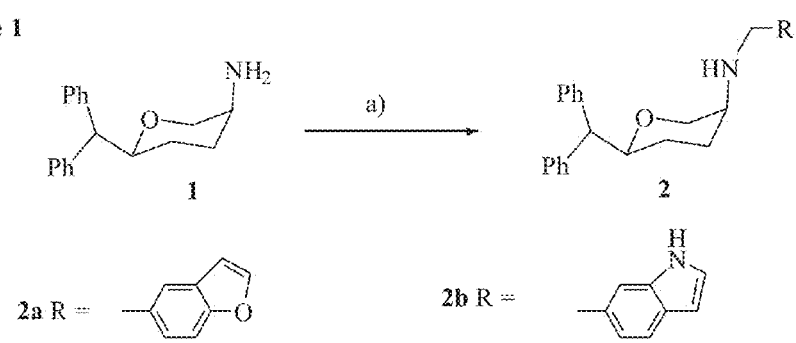
Figure 7:
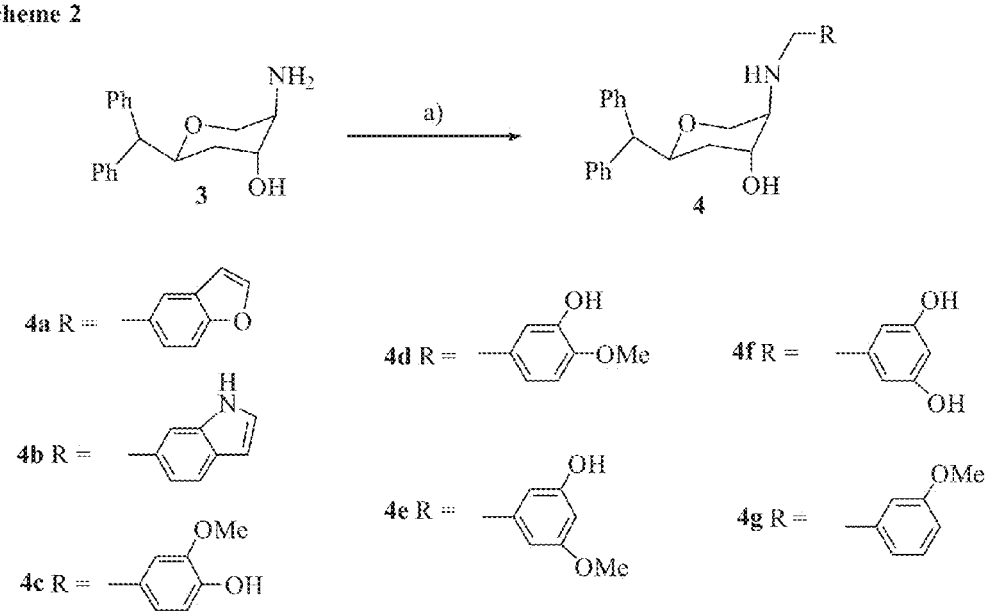
Figure 8:
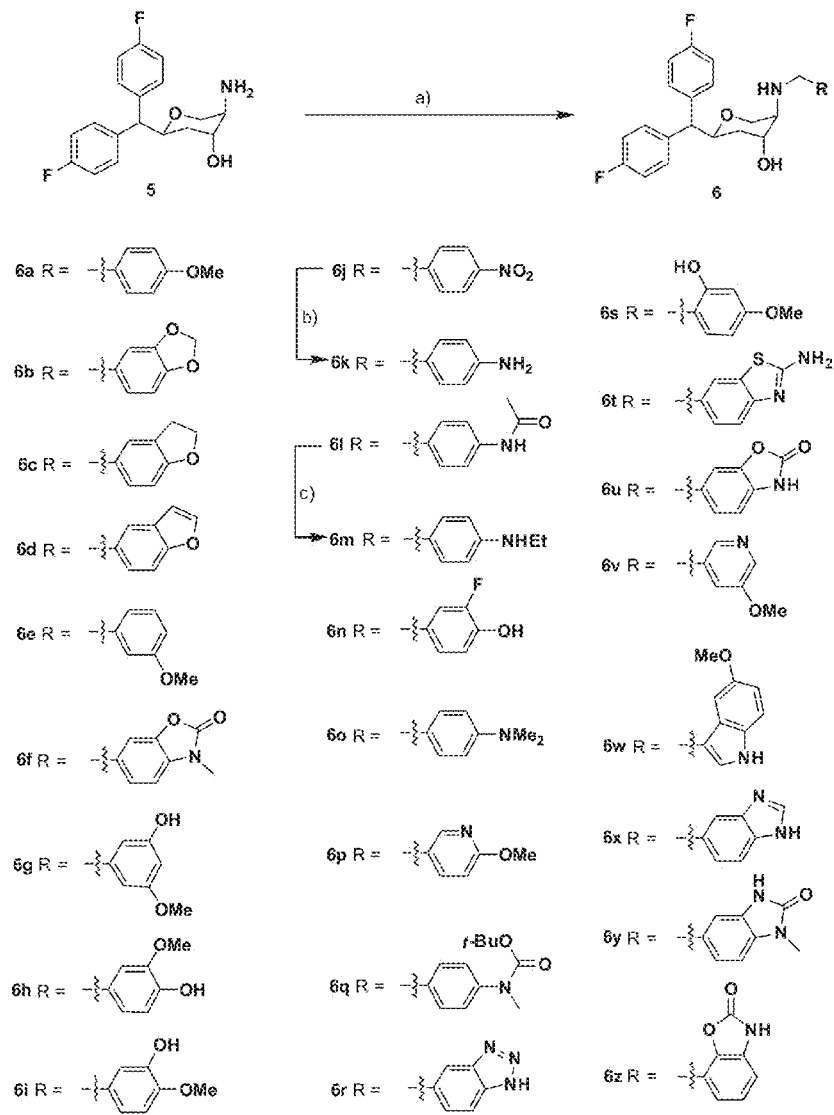
Figure 9:
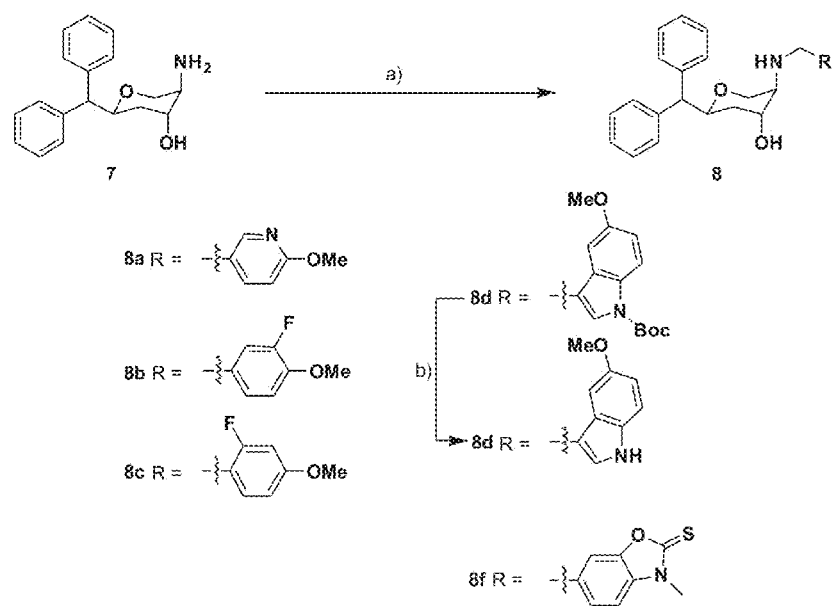
Figure 10:
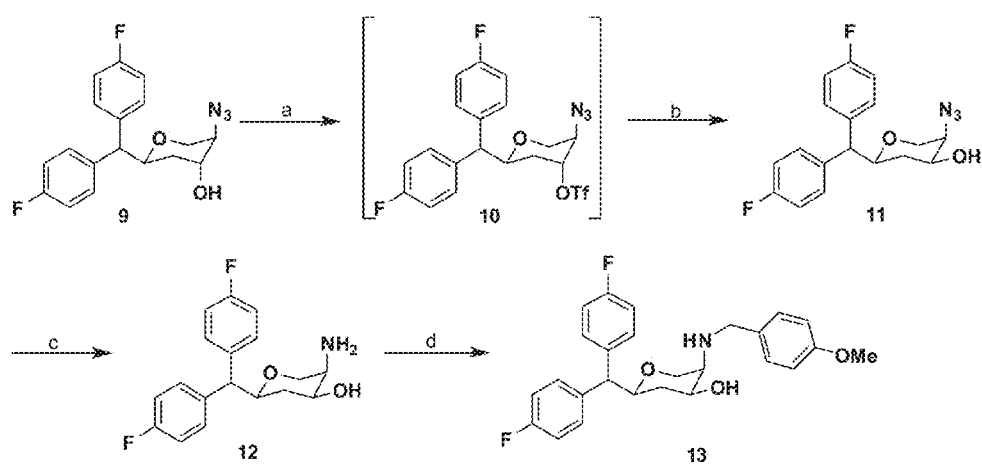

FIGS. 1A and 1B provide examples of functional groups attached to the pyran ring of the compound having formula I;

FIG. 2 provides examples of chemical structures of pyran derivatives;

FIG. 3 provides examples of chemical structures of pyran derivatives;

FIG. 4 provides examples of chemical structures of pyran derivatives;

FIG. 5 provides examples of chemical structures of pyran derivatives;

FIG. 6 provides synthetic Scheme 1;

FIG. 7 provides synthetic Scheme 2;

FIG. 8 provides synthetic Scheme 3;

FIG. 9 provides synthetic Scheme 4;

FIG. 10 provides synthetic Scheme 5; and

Figure 11:
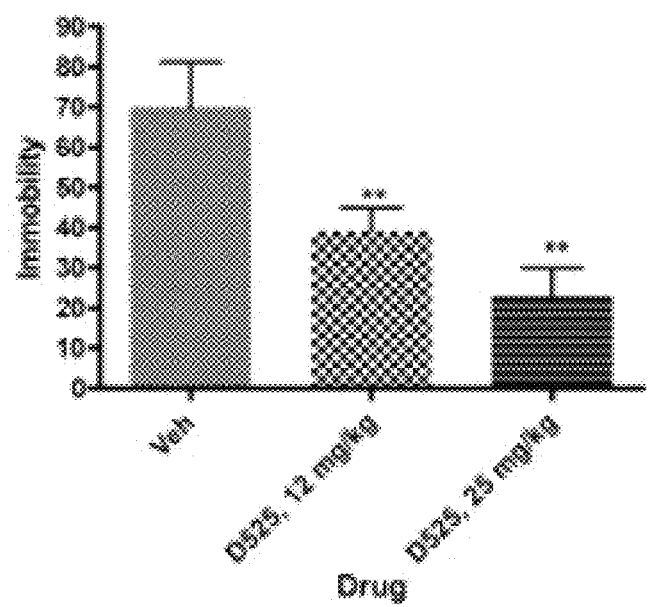

FIG. 11 provides a bar chart showing the effect of sub-chronic oral administration of vehicle and D-525 on the duration of immobility in the forced swimming test in rats. One way ANOVA analysis demonstrates significant effect among treatments: F (3,95)=8.12 (P<0.001). Dunnett's analysis showed that the effect of D-525 at two doses (12 and 25 mg/kg) immobility was statistically significant different compared to vehicle (P<0.01). Asterisks indicate a statistically significant difference toward control group that received saline p.o. **P<0.01. Each treatment group contained four to seven rats.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In an embodiment, certain 3,6-disubstituted and 2,4,5-trisubstituted pyran derivatives that exhibit potent activity on monoamine transport systems are provided. The 3,6 and 2,4,5 pyrans are useful in probing the effects of their binding to monoamine transporter systems and the corresponding relationships to various afflictions affecting the CNS, or as a treatment for various CNS-related disorders in which the monoamine transport and related systems are implicated. The present embodiment is an extension of the compounds set forth in U.S. Pat. No. 7,915,433, the entire disclosure of which is hereby incorporated by reference.

In an embodiment, a compound having formula I is provided.

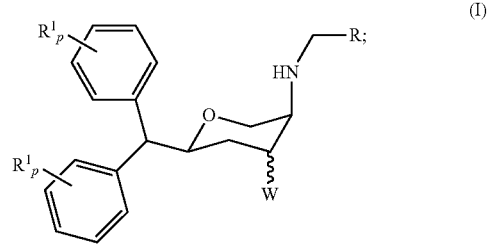

(I)

or a pharmaceutically acceptable derivative or salt thereof; wherein p=0 to 5;
R is an optionally substituted $C_6$-$C_{14}$ aryl or $C_4$-$C_{14}$ heteroaryl wherein heteroatoms of heteroaryl B are selected from the group consisting of O, N, and S. In a refinement, R is an $C_6$-$C_{14}$ aryl or $C_4$-$C_{14}$ heteroaryl having a substituent that includes O, N, and S;
p=0 to 5;
W is H, OH, or $NHR^o$;
$R^o$ is H or $C_{1-18}$ alkyl;

$R^1$ is $C_{1-4}$ alkyl, $C_{2-6}$ alkenyl, $C_{2-6}$ optionally halogenated alkynyl, $C_{2-6}$ hydroxyalkynyl, halo, —CN, —COOR$^2$, $C_{5-10}$ cycloalkyl, $C_{2-18}$ alkenyl, —OH, —NO$_2$, —NHR$^2$, or —OR$^2$; and $R^2$ is $C_{1-8}$ alkyl, $C_{5-6}$ cycloalkyl, or $C_{2-8}$ alkenyl;

In a refinement, R is:

wherein:

r is 0 to 5;

T is CH or N;

$R^3$ is F, Cl, Br, OR$^4$, NO$_2$, NHR$^4$, NH(CO)R$^4$, N(CO)OR$^4$, SO$_2$NH$_2$, or N(R$^4$)$_2$; and $R^4$ is H or $C_{1-8}$ alkyl.

In another refinement, R is:

where the dashed line is an optional bond forming a double bond therein;

X, Y, and Z are each independently CR$^4$, CR$^4{}_2$, C—NHR$^4$, C=O, S, N, or NR$^4$; and $R^4$ is H or $C_{1-8}$ alkyl. Additional examples for R are set forth in FIG. 1.

In a refinement, compounds having formula I are described by formula 2:

where

2a R =

2b R =

In a refinement, compounds having formula I are described by formula 4:

where

4a R =

4b R =

4c R =

4d R =

4e R =

4f R =

4g R =

In a refinement, compounds having formula I are described by formula 6:

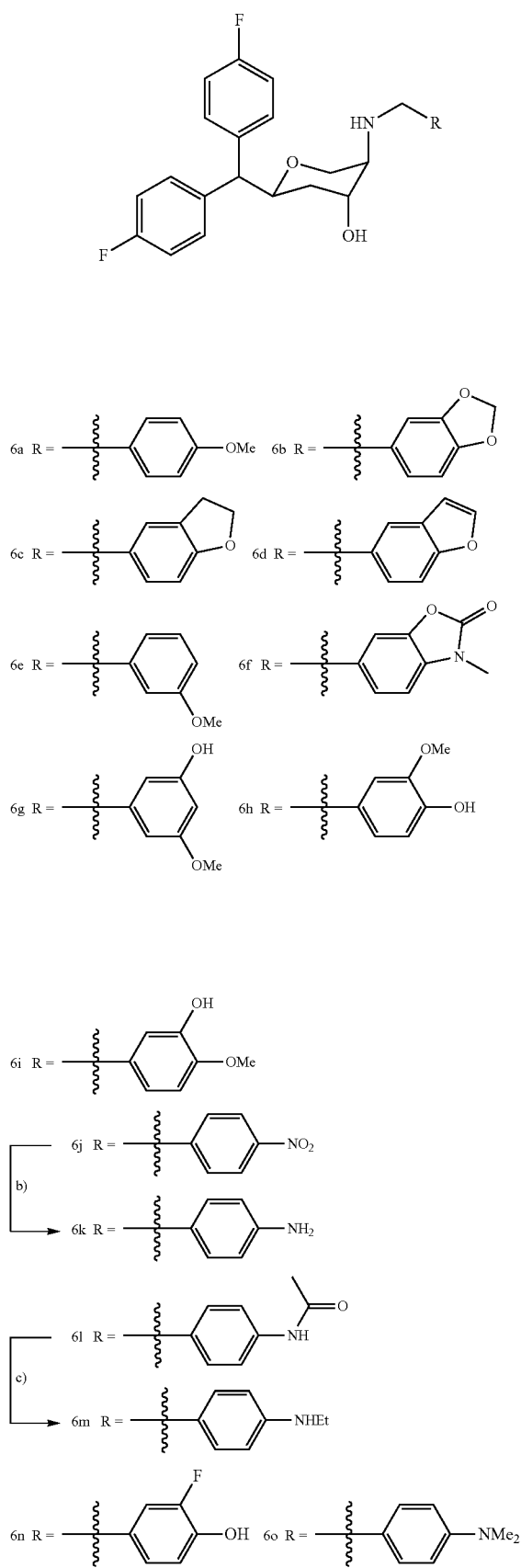
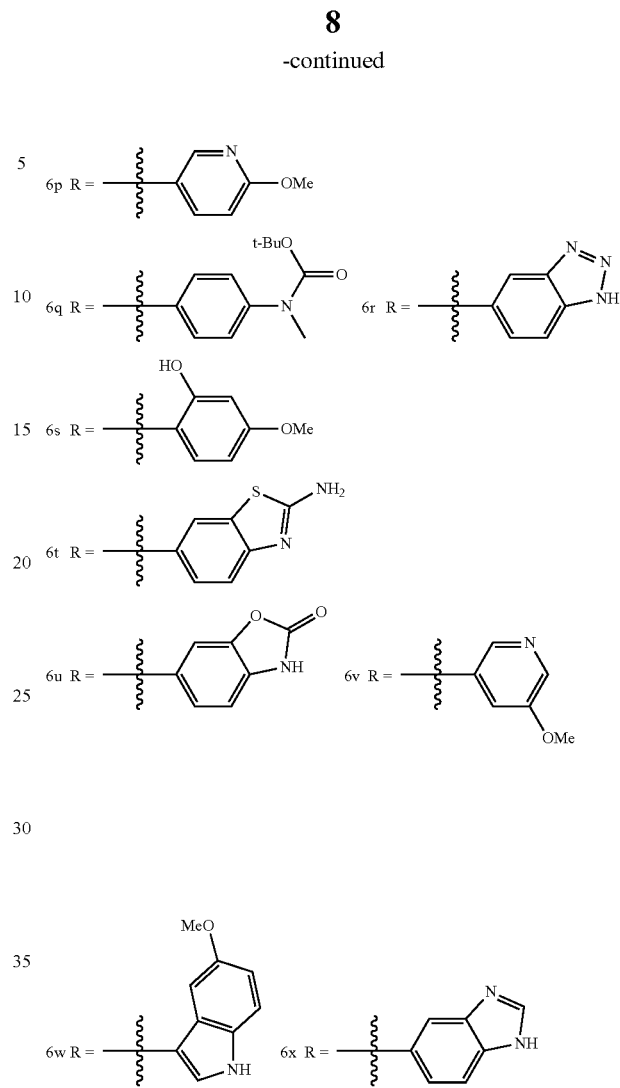
In a refinement, compounds having formula I are described by formula 8:
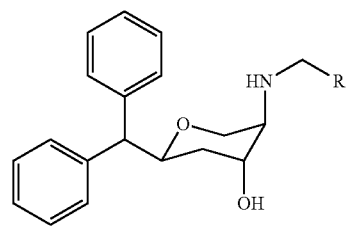

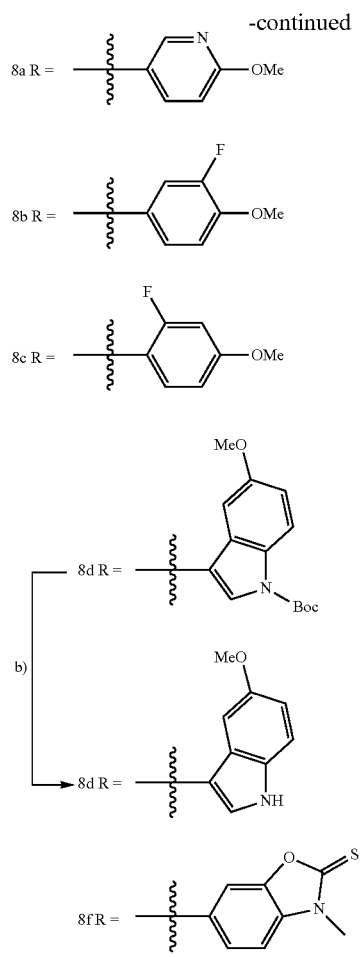

Examples of compounds having formula I include, but are not limited to, the compounds set forth in FIGS. 2-5.

The subject invention compounds may be used as such or in the form of their pharmaceutically acceptable derivatives and/or salts. By the term "derivative" is meant a chemically modified form of the "base compound" which will liberate an active form of the base compound or metabolite thereof following administration, and does not include salts of the base compound. However, derivatives may also, when appropriate, also be used in the form of salts. The particular type of derivative is dependent, in most cases, on the nature of functional group(s) present on the base compound or its salt, and selection of a suitable derivative is within the skill of the art. For example, when hydroxyl groups are present, ethers or esters are common derivatives, especially the latter, as are also carbamates.

In general, the derivative is hydrolyzable to the base compound in vivo or is enzymatically converted, in one or more steps, to the base compound (or a salt thereof). In the case of primary or secondary amino groups, common derivatives include amides, imides, ureas, and the like. Preparation of all these derivatives may take place by standard methods of organic chemistry. Simple esters may be produced from hydroxyl groups by esterification with a carboxylic acid, sulfonic acid, etc., a carboxylic acid anhydride, a carboxylic acid chloride, etc. Carbamates may be prepared by reaction with an organic isocyanate.

Further derivatives include inclusion compounds and clathrates, for example inclusion complexes formed from the contact of host molecules such as α, β, and γ-cyclodextrins, or chemically modified cyclodextrins well known to the art. Urea inclusion compounds are also derivatives. In these derivatives, the gurst molecules (base compounds) are not chemically bound, but are present due to molecular attraction, hydrogen bonding, surface energy effects, etc. In general, such complexes are stoichiometric, but non-stoichiometric complexes may also be used. Such complexes are easily prepared by one skilled in the art. For example, cyclodextrin complexes may be prepared by kneading together cyclodextrin and base compound in water followed by removal of free water.

Salts are most useful forms of the subject invention compounds, and are formed by the neutralization of basic nitrogen atoms in the base compound by an organic or inorganic acid. Useful organic acids are in particular carboxylic acids and sulfonic acids. Examples of mono-, di-, and polycarboxylic acids which are useful include formic acid, acetic acid, propionic acid, methane sulfonic acid, butyric acid, maleic acid, fumaric acid, malic acid, tartaric acid, citric acid, succinic acid, sulfosuccinic acid, tannic acid, and the like. An example of a sulfonic acid is toluene sulfonic acid. Examples of inorganic acids include hydrochloric acid, sulfuric acid, nitric acid, phosphoric acid, polyphosphoric acid, molybdic acid, nitrous acid, sulfurous acid, and the like. The salts are prepared by simply neutralizing the base compound all or in part, generally in aqueous solution. In such cases, water of hydration may be a part of the salt thus produced.

The compounds may be administered by any suitable technique, including intravenous administration, but are preferably administered in solid form, for example as a tablet or capsule, optionally in conjunction with conventional pharmaceutical additives such as tableting aids, lubricants, fillers, pH-adjusting substances, pH-regulating substances (buffers), emulsifiers, dispersing aids, antioxidants, UV-stabilizers, etc. Such ingredients are well known. The compositions may also be administered in other forms, such as syrups, dispersions, etc.

The dosage to be administered to a mammalian species is dependent on numerous factors such as the particular species, its weight, the type of disorder, the desired degree of treatment, and the individual itself. Dosages can be readily determined by one skilled in the art by routine tests, for example time/serum level measurements, dose/response curves, etc. The dosages are in particular easy to range, as numerous monoamine transport-affecting drugs are commercially available, have extensive in vitro and in vivo results presented in the literature, or are in clinical trials. This is true for both human and non-human subjects, anti-anxiety medication being common for use in domestic dogs and cats, for example.

Dosage ranges which are useful also vary with respect to the activity of the individual compounds, for example the binding data set forth below in Table 1, as well as whether the compound is administered in a fast or slow release formulation, its solubility, its rate of transfer into the plasma or into the extracellular space, etc. In a refinement, human doses are expected to be based on this data from 20 mg to 200 mg. However, activity is expected at doses as low as 2 mg or lower.

The following examples illustrate the various embodiments of the present invention. Those skilled in the art will recognize many variations that are within the spirit of the present invention and scope of the claims.

EXPERIMENTAL SECTION

FIGS. 6-10 provides synthetic schemes for the compounds of the present invention.

Reagents and solvents were obtained from commercial suppliers and used as received unless otherwise indicated. Dry solvents were obtained according to the standard procedures. All reactions were performed under inert atmosphere ($N_2$) unless otherwise noted. Analytical silica gel-coated TLC plates (silica gel 60 F254) were purchased from EM Science and were visualized with UV light or by treatment with either phosphomolybdic acid (PMA) or ninhydrin. Flash chromatography was carried out on Baker Silica Gel 40 μM. $^1$H NMR and $^{13}$C spectra were routinely recorded with a Varian 400 spectrometer operating at 400 and 100 MHz, respectively. The NMR solvent used was either $CDCl_3$ or $CD_3OD$ as indicated. TMS was used as an internal standard. NMR and rotation of free bases were recorded. Salts of free bases were used for biological characterization. Elemental analyses were performed by Atlantic Microlab Inc. and were within ±0.4% of the theoretical value. Optical rotations were recorded on a Perkin-Elmer 241 polarimeter.

Procedure A (3S,6S)-6-benzhydryl-N-(benzofuran-5-ylmethyl)tetrahydro-2H-pyran-3-amine (2a)

To a stirred solution of amine 1 (60 mg, 0.22 mmol) and 1-benzofuran-5-carbaldehyde (35 mg, 0.24 mmol) in 1,2-dichloroethane (6 mL) was added glacial acetic acid (13 μL, 0.22 mmol). After being stirred for 30 minutes, $NaCNBH_3$ (28 mg, 0.44 mmol) was added portion wise followed by methanol (1 mL). The reaction mixture was stirred for overnight. The reaction mixture was quenched with saturated $NaHCO_3$ solution at 0° C. and extracted with dichloromethane (3×75 mL). The combined organic layer was washed with water, brine, dried over $Na_2SO_4$, and the solvent was removed under reduced pressure. Crude product was purified by column chromatography using 70% ethylacetate in hexanes to give compound 2a (60 mg, 67%)) as thick syrup. $[\alpha]^{25}_D=(-)78.2°$ (c 0.5, MeOH). $^1$H NMR (400 MHz, $CDCl_3$): δ 1.25-1.38 (m, 1H), 1.50-1.70 (m, 2H), 1.82-2.02 (m, 1H), 2.68 (br s, 1H), 3.56 (dd, J=1.6, 12.0 Hz, 1H), 3.80-4.12 (m, 6H), 6.73 (d, J=1.2 Hz, 1H), 7.14-7.46 (m, 12H), 7.56 (s, 1H), 7.61 (d, J=2.0 Hz, 1H). $^{13}$C NMR (100 MHz, $CDCl_3$): δ 25.43, 27.76, 50.46, 50.98, 57.42, 70.40, 79.50, 106.75, 111.37, 120.78, 124.93, 126.47, 126.66, 127.70, 128.54, 128.74, 128.80, 135.11, 142.44, 142.70, 145.44, 154.42. The product was converted into the corresponding hydrochloride salt; mp: 140-142° C. Anal. ($C_{27}H_{27}NO_2·HCl·H_2O$) C, H, N.

((3S,6S)—N-((1H-indol-6-yl)methyl)-6-benzhydryltetrahydro-2H-pyran-3-amine (2b)

Compound 1 (50 mg, 0.19 mmol) was reacted with indole-6-carboxaldehyde (27 mg, 0.19 mmol), glacial acetic acid (13 μL, 0.22 mmol), and $NaCNBH_3$ (18 mg, 0.28 mmol) in 1,2-dichloroethane (6 mL) using procedure A. The residue was purified by column chromatography using 10% methanol in ethylacetate to afford compound 2b (50 mg, 66%) as a thick syrup. $[\alpha]^{25}_D=(-)78.4°$ (c 0.5, MeOH). $^1$H NMR (400 MHz, $CDCl_3$): δ 1.22-1.30 (m, 1H), 1.50-1.62 (m, 1H), 1.63-1.76 (m, 1H), 1.97-2.08 (m, 1H), 2.73 (s, 1H), 3.39 (d, J=12.0 Hz, 1H), 3.82-4.10 (m, 5H), 6.44 (s, 1H), 6.92-7.58 (m, 13H), 8.94 (s, 1H). $^{13}$C NMR (100 MHz, $CDCl_3$): δ 24.96, 26.17, 50.35, 50.56, 56.99, 68.99, 79.45, 102.18, 112.12, 120.67, 121.07, 125.30, 126.38, 126.72, 127.80, 128.50, 128.63, 128.76, 136.34, 142.34, 142.53. The product was converted into the corresponding oxalate salt; mp: 194-196° C. Anal. ($C_{27}H_{28}N_2O·C_2H_2O_4·H_2O$) C, H, N.

(2S,4R,5R)-2-benzhydryl-5-((benzofuran-5-ylmethyl)amino)tetrahydro-2H-pyran-4-ol (4a)

Compound 3 (60 mg, 0.21 mmol) was reacted with 1-benzofuran-5-carbaldehyde (34 mg, 0.23 mmol), glacial acetic acid (12 μL, 0.21 mmol), and $NaCNBH_3$ (26 mg, 0.42 mmol) in 1,2-dichloroethane (6 mL) using procedure A. The residue was purified by column chromatography using ethylacetate to afford compound 4a (60 mg, 69%) as a white solid. $[\alpha]^{25}_D=(-) 64.8°$ (c 0.5, MeOH). $^1$H NMR (400 MHz, $CDCl_3$): δ 1.43 (dt, J=3.2, 14.0 Hz, 1H), 1.70-1.80 (m, 1H), 2.48 (d, J=2.4 Hz, 1H), 3.76-3.84 (m, 2H), 3.88-4.16 (m, 4H), 4.51 (dt. J=2.4, 10.4 Hz, 1H), 6.73 (d, J=1.6 Hz, 1H), 7.12-7.38 (m, 11H), 7.44 (d, J=8.8 Hz, 1H), 7.52 (s, 1H), 7.61 (d, J=2.4 Hz, 1H). $^{13}$C NMR (100 MHz, $CDCl_3$): δ 33.68, 51.65, 56.74, 56.78, 65.05, 67.72, 73.85, 106.73, 111.45, 120.82, 124.90, 126.56, 126.76, 127.74, 128.62, 128.67, 128.87, 134.86, 142.27, 142.36, 145.53, 154.48. The product was converted into the corresponding hydrochloride salt; mp: 204-206° C. Anal. ($C_{27}H_{27}NO_3·HCl·H_2O$) C, H, N.

(2S,4R,5R)-5-(((1H-indol-6-yl)methyl)amino)-2-benzhydryltetrahydro-2H-pyran-4-ol (4b)

Compound 3 (50 mg, 0.18 mmol) was reacted with indole-6-caboxaldehyde (26 mg, 0.18 mmol), glacial acetic acid (12 μL, 0.21 mmol), and $NaCNBH_3$ (17 mg, 0.27 mmol) in 1,2-dichloroethane (6 mL) using procedure A. The residue was purified by column chromatography using 10% methanol in ethylacetate to afford compound 4b (60 mg, 82%) as a thick syrup. $[\alpha]^{25}_D=(-)59.6°$ (c 0.5, MeOH). $^1$H NMR (400 MHz, $CDCl_3$): δ 1.34-1.42 (m, 1H), 1.68-1.78 (m, 1H), 2.52 (s, 1H), 3.68-4.10 (m, 6H), 4.48 (t, J=9.6 Hz, 1H), 6.46 (s, 1H), 6.92-7.58 (m, 13H), 8.71 (s, 1H). $^{13}$C NMR (100 MHz, $CDCl_3$): δ 33.40, 51.45, 56.26, 56.74, 63.90, 66.34, 74.12, 102.43, 111.64, 120.92, 125.15, 126.57, 126.79, 127.71, 128.56, 128.59, 128.64, 128.90, 136.21, 142.14, 142.24. The product was converted into the corresponding oxalate salt; mp: 152-154° C. Anal. ($C_{27}H_{28}N_2O_2·C_2H_2O_4·H_2O$) C, H, N.

(2S,4R,5R)-2-benzhydryl-5-((4-hydroxy-3-methoxybenzyl)amino)tetrahydro-2H-pyran-4-ol (4c)

Compound 3 (60 mg, 0.21 mmol) was reacted with vanillin (39 mg, 0.25 mmol), glacial acetic acid (12 μL, 0.21 mmol), and $NaCNBH_3$ (26 mg, 0.42 mmol) in 1,2-dichloroethane (6 mL) using procedure A. The residue was purified by column chromatography using 5% methanol in ethylacetate to afford compound 4c (65 mg, 73%) as a thick syrup. $[\alpha]^{25}_D=(-)80.4°$ (c 0.5, MeOH). $^1$H NMR (400 MHz, $CDCl_3$): δ 1.38-1.48 (m, 1H), 1.68-1.78 (m, 1H), 2.52 (br s, 1H), 3.66 (d, J=12.8 Hz, 1H), 3.78 (s, 3H), 3.76-3.86 (m, 2H), 3.88-4.04 (m, 3H), 4.52 (dt, J=2.4, 8.0 Hz, 1H), 6.73 (d, J=8.0 Hz, 1H), 6.77 (d, J=8.4 Hz, 1H), 6.86 (s, 1H), 7.12-7.37 (m, 10H). $^{13}$C NMR (100 MHz, $CDCl_3$): δ 33.53, 51.18, 56.05, 56.63, 56.68, 64.30, 66.82, 74.02, 111.42, 114.78, 119.20, 121.56, 126.61, 126.82, 128.62, 128.66, 128.91, 142.23, 145.29, 147.09. The product was converted into the corresponding hydrochloride salt; mp: 203-205° C. Anal. ($C_{26}H_{29}NO_4·HCl·H_2O$) C, H, N.

(2S,4R,5R)-2-benzhydryl-5-((3-hydroxy-4-methoxybenzyl)amino)tetrahydro-2H-pyran-4-ol (4d)

Compound 3 (60 mg, 0.21 mmol) was reacted with 3-hydroxy-4-methoxybenzaldehyde (39 mg, 0.25 mmol), glacial acetic acid (12 μL, 0.21 mmol), and $NaCNBH_3$ (26 mg, 0.42 mmol) in 1,2-dichloroethane (6 mL) using procedure A. The residue was purified by column chromatography using 5% methanol in ethylacetate to afford compound 4d (65 mg, 73%) as a thick syrup. [α]$^{25}_D$=(−)78.4° (c 0.5, MeOH). $^1$H NMR (400 MHz, CDCl$_3$+MeOH-d$_4$): δ 1.36-1.44 (m, 1H), 1.54-1.64 (m, 1H), 2.45 (d, J=2.8 Hz, 1H), 2.85 (br s, 3H), 3.58 (d, J=12.8 Hz, 1H), 3.72-3.78 (m, 2H), 3.81 (s, 3H), 3.84-3.94 (m, 3H), 4.47 (dt, J=2.4, 10.8 Hz, 1H), 6.69 (dd, J=1.6, 8.4 Hz, 1H), 6.74 (d, J=8.0 Hz, 1H), 6.83 (d, J=1.6 Hz, 1H), 7.08-7.32 (m, 10H). The product was converted into the corresponding hydrochloride salt; mp: 168-170° C. Anal. (C$_{26}$H$_{29}$NO$_4$.HCl.H$_2$O) C, H, N.

(2S,4R,5R)-2-benzhydryl-5-((3-hydroxy-5-methoxybenzyl)amino)tetrahydro-2H-pyran-4-ol (4e)

Compound 3 (60 mg, 0.21 mmol) was reacted with 3-hydroxy-5-methoxybenzaldehyde (38 mg, 0.25 mmol), glacial acetic acid (12 μL, 0.21 mmol), and NaCNBH$_3$ (26 mg, 0.42 mmol) in 1,2-dichloroethane (6 mL) using procedure A. The residue was purified by column chromatography using 5% methanol in ethylacetate to afford compound 4e (65 mg, 73%) as a thick syrup. [α]$^{25}_D$=(−)75.6° (c 0.5, MeOH). $^1$H NMR (400 MHz, CDCl$_3$): δ 1.34-1.42 (m, 1H), 1.52-1.64 (m, 1H), 2.41 (br s, 1H), 3.52 (d, J=13.2 Hz, 1H), 3.64 (s, 3H), 3.60-3.75 (m, 2H), 3.78-3.93 (m, 2H), 4.45 (dt, J=1.6, 10.0 Hz, 1H), 4.56 (br s, 2H), 6.26 (s, 1H), 6.32 (s, 1H), 6.33 (s, 1H), 7.10-7.32 (m, 10H). $^{13}$C NMR (100 MHz, CDCl$_3$): δ 33.35, 50.85, 55.47, 56.34, 56.51, 63.94, 66.58, 74.14, 101.09, 106.51, 108.32, 126.67, 126.86, 128.54, 128.71, 128.94, 140.79, 142.04, 142.18, 158.00, 161.25. The product was converted into the corresponding hydrochloride salt; mp: 160-162° C. Anal. (C$_{26}$H$_{29}$NO$_4$.HCl.H$_2$O) C, H, N.

5-(((((3R,4R,6S)-6-benzhydryl-4-hydroxytetrahydro-2H-pyran-3-yl)amino)methyl)benzene-1,3-diol (4f)

Compound 3 (60 mg, 0.21 mmol) was reacted with 3,5-dihydroxybenzaldehyde (29 mg, 0.21 mmol), glacial acetic acid (12 μL, 0.21 mmol), and NaCNBH$_3$ (26 mg, 0.42 mmol) in 1,2-dichloroethane (6 mL) using procedure A. The residue was purified by column chromatography using 7% methanol in dichloromethane to afford compound 4f (65 mg, 76%) as a thick syrup. [α]$^{25}_D$=(−)74.2° (c 0.5, MeOH). $^1$H NMR (400 MHz, CDCl$_3$): δ 1.34-1.42 (m, 1H), 1.55 (dt, J=2.4, 10.8 Hz, 1H), 2.43 (br s, 1H), 3.30 (s, 1H), 3.51 (d, J=12.8 Hz, 1H), 3.60-3.70 (m, 2H), 3.78-3.90 (m, 3H), 4.31 (br s, 3H), 4.45 (t, J=8.4 Hz, 1H), 6.16 (s, 1H), 6.21 (s, 1H), 6.22 (s, 1H), 7.02-7.28 (m, 10H). $^{13}$C NMR (100 MHz, CDCl$_3$): δ 33.06, 50.68, 55.99, 56.73, 63.94, 65.73, 74.08, 102.18, 107.35, 126.51, 126.72, 128.46, 128.48, 128.55, 128.77, 139.97, 141.97, 142.18, 158.26. The product was converted into the corresponding hydrochloride salt; mp: 168-170° C. Anal. (C$_{25}$H$_{27}$NO$_4$.HCl.H$_2$O) C, H, N.

(2S,4R,5R)-2-benzhydryl-5-((3-methoxybenzyl)amino)tetrahydro-2H-pyran-4-ol (4g)

Compound 3 (60 mg, 0.21 mmol) was reacted with 3-methoxybenzaldehyde (35 mg, 0.25 mmol), glacial acetic acid (12 μL, 0.21 mmol), and NaCNBH$_3$ (27 mg, 0.42 mmol) in 1,2-dichloroethane (6 mL) using procedure A. The residue was purified by column chromatography using 3% methanol in ethylacetate to afford compound 4g (65 mg, 76%) as a thick syrup. [α]$^{25}_D$=(−) 84.2° (c 0.5, MeOH). $^1$H NMR (400 MHz, CDCl$_3$): δ 1.38-1.46 (m, 1H), 1.66-1.78 (m, 1H), 2.16 (br s, 2H), 2.44 (d, J=2.4 Hz, 1H), 3.70 (d, J=13.6 Hz, 1H), 3.76-3.82 (m, 1H), 3.79 (s, 3H), 3.84-3.98 (m, 4H), 4.50 (dt, J=2.4, 10.4 Hz, 1H), 6.80 (dd, J=1.6, 8.0 Hz, 1H), 6.86-6.92 (m, 2H), 7.14-7.38 (m, 11H), $^{13}$C NMR (100 MHz, CDCl$_3$): δ 33.40, 51.26, 55.22, 56.50, 56.64, 64.76, 67.30, 73.61, 112.53, 113.64, 120.43, 126.35, 126.55, 128.40, 128.66, 129.45, 141.64, 142.04, 142.10, 159.75. The product was converted into the corresponding hydrochloride salt; mp: 197-199° C. Anal. (C$_{26}$H$_{29}$NO$_3$.HCl) C, H, N.

Synthesis of (2S,4R,5R)-2-(bis(4-fluorophenyl)methyl)-5-((4-methoxybenzyl)amino)tetrahydro-2H-pyran-4-ol

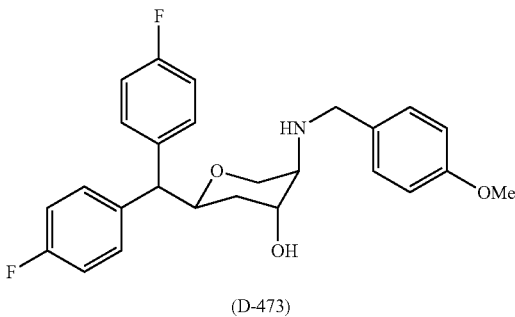

6a (D-473)

Amine 5 (200 mg, 0.63 mmol) was reacted with 4-methoxybenzaldehyde (90 mg, 0.66 mmol), glacial acetic acid (25 μL, 0.41 mmol), and Na(OAc)$_3$BH (199 mg, 0.93 mmol) in a mixture of 1,2-dichloroethane (6 mL) and methanol (2 mL). The residue was purified by gradient silica gel column chromatography using a mixture of dichloromethane and methanol (100:1 to 6:1) to afford corresponding compound 6j (200 mg, 73%) as a white solid
$^1$H NMR (400 MHz, CDCl$_3$): δ 7.06-7.39 (m, 6H), 6.94 (dd, J=16.7, 8.5 Hz, 4H), 6.84 (d, J=7.9 Hz, 2H), 4.39 (t, J=9.4 Hz, 1H), 4.04 (s, 1H), 3.59-4.0 (m, 8H), 2.62 (s, 1H), 1.68 (t, J=11.43 Hz, 1H), 1.41 (d, J=14.1 Hz, 1H).
$^{13}$C NMR (100 MHz, CDCl$_3$): δ 162.7, 162.6, 160.3, 160.2, 159.4, 137.5, 137.4, 137.3, 137.2, 129.9, 129.8, 129.7, 129.6, 128.3, 115.6, 115.4, 115.3, 115.1, 114.2, 73.8, 65.6, 63.6, 56.3, 55.3, 54.6, 50.3, 32.9.
[α]$^{25}_D$=(−)48.7°, c=1 in MeOH. The product was converted into corresponding hydrochloride salt, m.p.: 190-205° C. Anal. Calcd for [C$_{26}$H$_{27}$F$_2$NO$_3$.HCl.H$_2$O] C, H, N.
The product was converted into corresponding mesylate salt, m.p.: 200-205° C. Anal. Calcd for [C$_{26}$H$_{27}$F$_2$NO$_3$.CH$_3$SO$_3$H] C, H, N.

Synthesis of (2S,4R,5R)-5-((benzo[d][1,3]dioxol-5-ylmethyl)amino)-2-(bis(4-fluorophenyl)methyl)tetrahydro-2H-pyran-4-ol

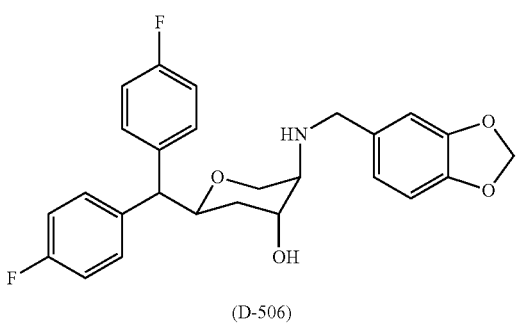

6b (D-506)

Amine 5 (40 mg, 0.13 mmol) was reacted with 4-nitrobenzaldehyde (23 mg, 0.15 mmol), glacial acetic acid (13 µL, 0.21 mmol), and NaCNBH$_3$ (14 mg, 0.22 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6b (D-506) (47 mg, 84%) as a colorless syrup.

$^1$H NMR (400 MHz, CDCl$_3$): δ 7.23-7.32 (m 2H), 7.11-7.19 (m, 2H), 6.90-7.02 (m, 4H), 6.82 (s, 1H), 6.67-6.78 (m, 2H), 5.92 (s, 2H), 4.29-4.46 (m, 1H), 3.84-4.0 (m, 3H), 3.70-3.82 (m, 2H), 3.61 (d, J=12.9 Hz, 1H), 2.42 (s, 1H), 1.99 (br s, 1H), 1.61-1.73 (m, 1H), 1.32-1.42 (m, 1H).

$^{13}$C NMR (100 MHz, CDCl$_3$): δ 162.7, 162.6, 160.3, 160.2, 147.7, 146.6, 137.7, 137.4, 133.9, 129.9, 129.8, 129.7, 129.6, 121.1, 115.6, 115.3, 115.3, 115.1, 108.5, 108.0, 100.9, 73.5, 67.3, 64.9, 56.2, 51.1, 33.2.

$[\alpha]^{25}_D$=(−)23.9°, c=1 in MeOH. The product was converted into the corresponding hydrochloride salt; mp: 150-155° C. Anal. Calcd for [C$_{26}$H$_{25}$F$_2$NO$_4$.HCl] C, H, N.

Synthesis of (2S,4R,5R)-2-(bis(4-fluorophenyl)methyl)-5-(((2,3-dihydrobenzofuran-5-yl)methyl)amino)tetrahydro-2H-pyran-4-ol

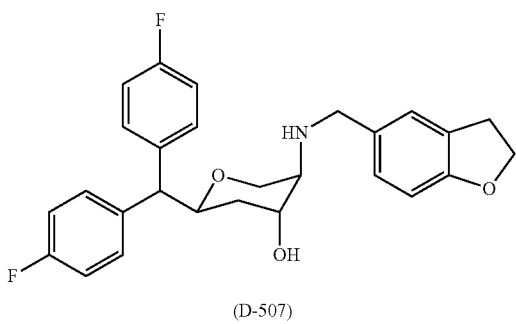

(D-507)

Amine 5 (50 mg, 0.16 mmol) was reacted with 2,3-dihydrobenzofuran-5-carbaldehyde (28 mg, 0.19 mmol), glacial acetic acid (13 µL, 0.21 mmol), and NaCNBH$_3$ (17 mg, 0.27 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6c (D-507) (56 mg, 79%) as a light yellow syrup.

$^1$H NMR (400 MHz, CDCl$_3$): δ 7.23-7.31 (m, 2H), 7.10-7.19 (m, 3H), 6.89-7.03 (m, 5H), 6.71 (d, J=8.1 Hz, 1H), 4.55 (t, J=8.8 Hz, 2H), 4.33-4.47 (m, 1H), 3.95-4.03 (m, 1H), 3.85-3.94 (m, 2H), 3.74-3.83 (m, 2H), 3.63 (d, J=12.7 Hz, 1H), 3.17 (t, J=8.8 Hz, 2H), 2.46 (s, 1H), 1.63-1.74 (m, 1H), 1.36-1.46 (m, 1H).

$^{13}$C NMR (100 MHz, CDCl$_3$): δ 162.7, 162.6, 160.3, 160.2, 159.3, 137.8, 137.7, 137.5, 137.4, 131.8, 129.9, 129.8, 129.7, 129.6, 127.9, 127.2, 124.9, 115.6, 115.4, 115.3, 115.1, 108.9, 73.5, 71.3, 67.2, 64.7, 56.3, 54.9, 51.0, 33.2, 29.7.

$[\alpha]^{25}_D$=(−)39.8°, c=1 in CH$_2$Cl$_2$. The product was converted into the corresponding hydrochloride salt; mp: 145-150° C. Anal. Calcd for [C$_{27}$H$_{27}$F$_2$NO$_3$.HCl] C, H, N.

Synthesis of Benzofuran-5-carbaldehyde

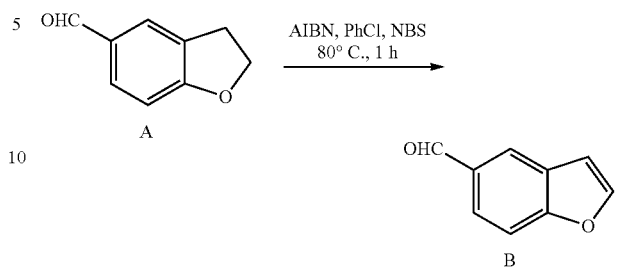

To a solution of 2,3-dihydrobenzofuran-5-carbaldehyde (1 g, 6.75 mmol, A) in Chlorobenzene (20 mL), NBS (1.44 g, 8.10 mmol), AIBN (22 mg, 0.13 mmol) were added and the mixture was stirred at 80° C. for 1 h. After cooling the reaction mixture to room temperature, it was washed with aqueous NaHCO$_3$. The organic layer was separated and the aqueous layer was washed with CH$_2$Cl$_2$. The organic layers were combined, dried over Na$_2$SO$_4$ and concentrated under vacuum on a rotary evaporator. The crude product was purified via gradient column chromatography using hexanes and ethyl acetate (100:1 to 1:1) to obtain the desired aldehyde B as brown syrup (60%) which solidifies at 0° C.

$^1$H NMR (500 MHz, CDCl$_3$): δ 10.07 (s, 1H), 8.15 (d, J=1.2 Hz, 1H), 7.87 (dd, J=1.5, 8.6 Hz, 1H), 7.73 (d, J=2.4 Hz, 1H), 7.62 (d, J=8.5 Hz, 1H), 6.90 (m, 1H).

$^{13}$C NMR (125 MHz, CDCl$_3$): δ 191.7, 158.2, 146.7, 132.2, 125.7, 124.6, 112.1, 107.2.

Synthesis of (2S,4R,5R)-5-((benzofuran-5-ylmethyl)amino)-2-(bis(4-fluorophenyl)methyl)tetrahydro-2H-pyran-4-ol

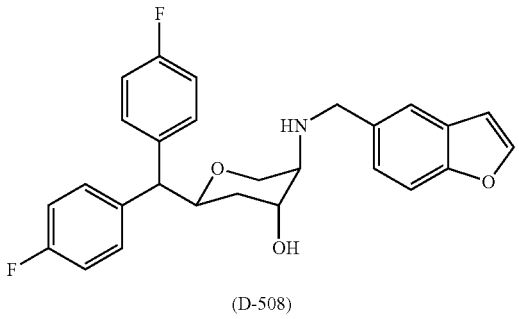

(D-508)

Amine 5 (50 mg, 0.16 mmol) was reacted with benzofuran-5-carbaldehyde (27 mg, 0.19 mmol), glacial acetic acid (13 µL, 0.21 mmol), and NaCNBH$_3$ (17 mg, 0.27 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6d (D-508) (55 mg, 81%) as a light yellow syrup.

$^1$H NMR (500 MHz, CDCl$_3$): δ 7.61 (d, J=2.1 Hz, 1H), 7.51 (s, 1H), 7.43 (d, J=8.5 Hz, 1H), 7.25-7.30 (m, 2H), 7.23 (d, J=8.5 Hz, 1H), 7.11-7.18 (m, 2H), 6.91-7.03 (m, 4H), 6.69-6.75 (m, 1H), 4.34-4.44 (m, 1H), 3.97-4.03 (m, 4H), 3.81 (d, J=12.8 Hz, 2H), 2.48 (s, 1H), 1.65-1.77 (m, 1H), 1.40 (d, J=14.4 Hz, 1H).

$^{13}$C NMR (125 MHz, CDCl$_3$): δ 162.5, 162.4, 160.6, 160.5, 154.2, 145.3, 137.7, 137.6, 137.5, 137.4, 134.6, 129.9, 129.8, 129.7, 129.6, 127.5, 124.6, 120.5, 115.5, 15.4, 115.3, 115.1, 111.2, 106.4, 73.5, 67.4, 64.9, 56.3, 54.9, 51.4, 33.2.

[α]$^{25}_D$=(-)39.3°, c=1 in CH$_2$Cl$_2$. The product was converted into the corresponding hydrochloride salt; mp: 160-165° C. Anal. Calcd for [C$_{27}$H$_{25}$F$_2$NO$_3$.HCl] C, H, N.

Synthesis of (2S,4R,5R)-2-(bis(4-fluorophenyl)methyl)-5-((3-methoxybenzyl)amino)tetrahydro-2H-pyran-4-ol

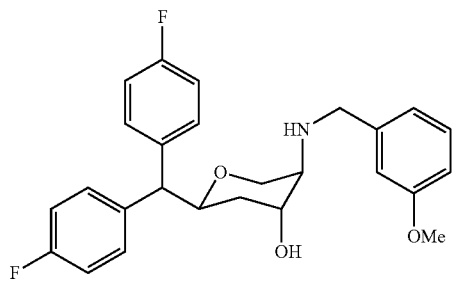

(D-524)

Amine 5 (126 mg, 0.40 mmol) was reacted with 3-methoxybenzaldehyde (31 mg, 0.23 mmol), glacial acetic acid (16 μL, 0.26 mmol), and NaCNBH$_3$ (20 mg, 0.32 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6e (D-524) (55 mg, 66%) as a colorless syrup.

$^1$H NMR (400 MHz, CDCl$_3$): δ 7.10-7.36 (m, 5H), 6.83-7.03 (m, 6H), 6.75-6.83 (m, 1H), 4.33-4.45 (m, 1H), 3.65-4.01 (m, 9H), 2.45 (s, 1H), 1.98 (br s, 1H), 1.64-1.77 (m, 1H), 1.39-1.48 (m, 1H).

$^{13}$C NMR (100 MHz, CDCl$_3$): δ 162.7, 162.6, 160.3, 160.2, 159.7, 141.7, 137.7, 137.4, 129.9, 129.8, 129.7, 129.6, 129.4, 120.3, 115.6, 115.4, 115.3, 115.1, 113.6, 112.4, 73.5, 67.3, 64.9, 56.3, 55.2, 54.9, 51.2, 33.2.

[α]$^{25}_D$=(-)77.6°, c=1 in CH$_2$Cl$_2$. The product was converted into the corresponding hydrochloride salt; mp: 190-195° C. Anal. Calcd for [C$_{26}$H$_{27}$F$_2$NO$_3$.HCl] C, H, N.

Synthesis of 3-methyl-2-oxo-2,3-dihydrobenzo[d]oxazole-6-carbaldehyde

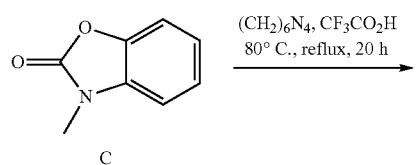

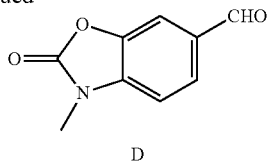

D

3-Methyl-2(3H)-benzoxazolone (3.6 g, 24.13 mmol, C) was taken in an oven dried RB flask equipped with magnetic stir bar. To the flask, hexamethylenetetramine (10.15 g, 72.38 mmol) was added, followed by TFA (36 mL). The resulting mixture was refluxed at 80° C. for about 20 h. The reaction mixture was then cooled and poured into ice-water. The solution was then basified with saturated NaHCO$_3$ and extracted with ethyl acetate. The aqueous layer was extracted further with ethyl acetate. The organic layers were combined, dried over Na$_2$SO$_4$ and concentrated under reduced pressure on a rotary evaporator to obtain the desired aldehyde D as yellow solid (70%).

$^1$H NMR (400 MHz, CDCl$_3$): δ 9.93 (s, 1H), 7.74-7.79 (m, 1H), 7.73 (s, 1H), 7.11 (d, J=8.1 Hz, 1H), 3.46 (s, 3H).

$^{13}$C NMR (100 MHz, CDCl$_3$): δ 190.3, 154.4, 142.9, 136.9, 131.8, 128.3, 109.5, 107.9, 28.4.

Synthesis of 6-((((3R,4R,6S)-6-(bis(4-fluorophenyl)methyl)-4-hydroxytetrahydro-2H-pyran-3-yl)amino)methyl)-3-methylbenzo[d]oxazol-2(3H)-one

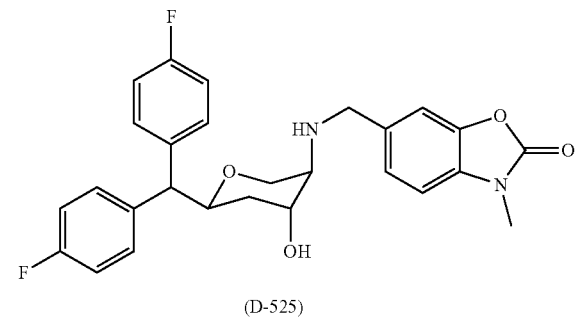

(D-525)

Amine 5 (50 mg, 0.16 mmol) was reacted with 3-methyl-2-oxo-2,3-dihydrobenzo[d]oxazole-6-carbaldehyde (33 mg, 0.19 mmol), glacial acetic acid (16 μL, 0.26 mmol), and NaCNBH$_3$ (17 mg, 0.27 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6f (D-525) (55 mg, 73%) as a white solid.

$^1$H NMR (400 MHz, CDCl$_3$): δ 7.23-7.32 (m, 2H), 7.21 (s, 1H), 7.07-7.18 (m, 3H), 6.90-7.01 (m, 4H), 6.87 (d, J=7.8 Hz, 1H), 4.35-4.45 (m, 1H), 3.84-4.01 (m, 4H), 3.69-3.82 (m, 2H), 3.37 (s, 3H), 2.44 (br d, J=2.0 Hz, 1H), 2.31 (br s, 1H), 1.62-1.75 (m, 1H), 1.37-1.45 (m, 1H).

$^{13}$C NMR (100 MHz, CDCl$_3$): δ 162.7, 162.6, 160.3, 160.2, 154.9, 142.8, 137.6, 137.4, 130.7, 129.9, 128.8, 127.7, 129.6, 123.5, 115.5, 115.3, 115.2, 115.1, 109.7, 107.7, 73.5, 67.1, 64.8, 56.2, 55.0, 51.0, 33.2, 28.1.

[α]$^{25}_D$=(-)59.1°, c=1 in CH$_2$Cl$_2$. The product was converted into the corresponding hydrochloride salt; mp: 235-

240° C. Anal. Calcd for [C$_{27}$H$_{26}$F$_2$N$_2$O$_4$.HCl] C, H, N. The product was converted into the corresponding mesylate salt; mp: 140-145° C. Anal. Calcd for [C$_{27}$H$_{26}$F$_2$N$_2$O$_4$.CH$_3$SO$_3$H.H$_2$O] C, H, N.

Synthesis of 3-hydroxy-5-methoxybenzaldehyde

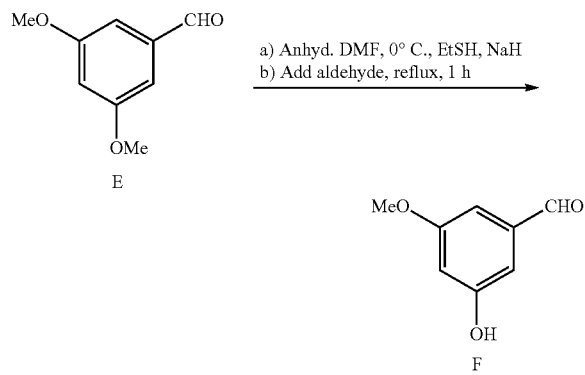

NaH (2.72 g, 71.4 mmol, 60% in mineral oil) was taken in an oven-dried RB flask equipped with magnetic stir bar and anhydrous DMF (60 mL) was added. After cooling the solution at 0° C., ethanethiol (7 mL, 93.4 mmol) was slowly added via a syringe, once the evolution of H$_2$ ceased, it was refluxed under N$_2$ atmosphere for 1 h. Next, aldehyde E (3.84 g, 23.6 mmol) in DMF (90 mL) was added and the resulting solution was refluxed under N$_2$ atmosphere for 1 h. The reaction mixture was then cooled and quenched by the addition of saturated aqueous NaCl (750 mL), 26% formaline (75 mL), and acetic acid (140 mL). The reaction mixture was then thoroughly extracted with ethyl acetate, the organic layer was dried over Na$_2$SO$_4$ and concentrated under vacuum to obtain a crude dark syrup. The crude syrup was purified by gradient column chromatography using hexanes and ethyl acetate (100:1 to 1:1) to afford the desired aldehyde F as a yellow solid (70%).

$^1$H NMR (500 MHz, CDCl$_3$): δ 9.84 (s, 1H, —CHO), 6.96 (d, J=2.5 Hz, 2H), 6.68 (t, J=2.1 Hz, 1H), 3.83 (s, 3H).

$^{13}$C NMR (125 MHz, CDCl$_3$): δ 192.8, 161.2, 158.6, 138.1, 109.2, 108.2, 106.0, 55.4.

Synthesis of (2S,4R,5R)-2-(bis(4-fluorophenyl) methyl)-5-((3-hydroxy-5-methoxybenzyl)amino) tetrahydro-2H-pyran-4-ol

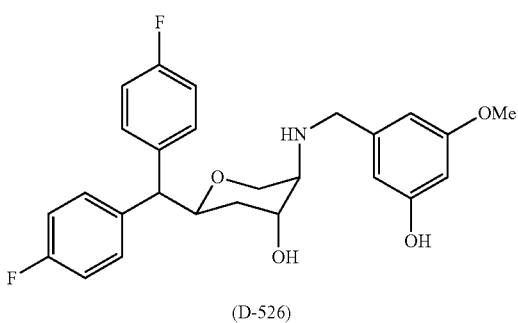

(D-526)

Amine 5 (50 mg, 0.16 mmol) was reacted with 3-hydroxy-5-methoxybenzaldehyde (29 mg, 0.19 mmol), glacial acetic acid (13 μL, 0.21 mmol), and Na(OAc)$_3$BH (125 mg, 0.59 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6g (526) (65 mg, 76%) as a colorless syrup.

$^1$H NMR (400 MHz, CDCl$_3$): δ 7.17-7.24 (m, 2H), 7.02-7.12 (m, 2H), 6.83-6.98 (m, 4H), 6.42 (s, 1H), 6.34 (s, 1H), 6.26 (s, 1H), 4.60 (br s, 1H), 4.37 (t, J=9.1 Hz, 1H), 4.07 (s, 1H), 3.82-3.94 (m, 2H), 3.71-3.81 (m, 2H), 3.67 (s, 3H), 3.63 (d, J=13.2 Hz, 1H), 2.56 (s, 1H), 1.65 (t, J=11.5 Hz, 1H), 1.39 (d, J=14.9 Hz, 1H).

$^{13}$C NMR (100 MHz, CDCl$_3$): δ 162.8, 162.7, 161.1, 160.3, 160.2, 157.8, 139.1, 137.4, 129.7, 115.6, 115.4, 115.1, 108.1, 106.6, 101.1, 73.9, 65.7, 63.4, 56.2, 55.2, 54.5, 50.4, 32.9.

$[α]^{25}_D$=(−)46.4°, c=1 in CH$_2$Cl$_2$. The product was converted into the corresponding hydrochloride salt; mp: 150-155° C. Anal. Calcd for [C$_{26}$H$_{27}$F$_2$NO$_4$.HCl.H$_2$O] C, H, N.

Synthesis of (2S,4R,5R)-2-(bis(4-fluorophenyl) methyl)-5-((4-hydroxy-3-methoxybenzyl)amino) tetrahydro-2H-pyran-4-ol

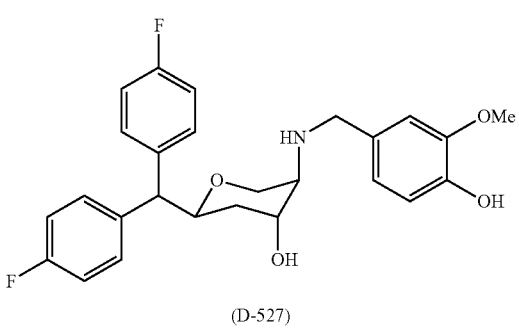

(D-527)

Amine 5 (60 mg, 0.19 mmol) was reacted with 3-hydroxy-4-methoxybenzaldehyde (34 mg, 0.23 mmol), glacial acetic acid (17 μL, 0.28 mmol), and NaCNBH$_3$ (20 mg, 0.32 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6h (D-527) (65 mg, 76%) as a colorless syrup.

$^1$H NMR (400 MHz, CDCl$_3$): δ 7.26 (dd, J=8.2, 5.6 Hz, 2H), 7.14 (dd, J=8.5, 5.6 Hz, 2H), 6.89-7.20 (m, 4H), 6.78-6.88 (m, 2H), 6.71-6.77 (m, 1H), 4.34-4.46 (m, 1H), 4.0-4.08 (m, 1H), 3.76-3.97 (m, 7H), 3.67 (d, J=12.9 Hz, 1H), 2.51 (s, 1H), 1.64-1.77 (m 1H), 1.37-1.48 (m, 1H).

$^{13}$C NMR (100 MHz, CDCl$_3$): δ 162.7, 162.6, 160.3, 146.7, 144.9, 137.6, 137.4, 130.7, 129.9, 129.8, 129.7, 129.5, 121.2, 115.6, 115.4, 115.3, 115.1, 114.3, 110.9, 73.6, 66.8, 64.3, 56.3, 55.8, 54.8, 50.9, 33.1.

$[α]^{25}_D$=(−)28.7°, c=1 in MeOH. The product was converted into the corresponding hydrochloride salt; mp: 190-195° C. Anal. Calcd for [C$_{26}$H$_{27}$F$_2$NO$_4$.HCl.H$_2$O] C, H, N.

Synthesis of (2S,4R,5R)-2-(bis(4-fluorophenyl)methyl)-5-((3-hydroxy-4-methoxybenzyl)amino)tetrahydro-2H-pyran-4-ol 6i (D-528)

Amine 5 (60 mg, 0.19 mmol) was reacted with 3-hydroxy-4-methoxybenzaldehyde (34 mg, 0.23 mmol), glacial acetic acid (17 µL, 0.28 mmol), and NaCNBH$_3$ (20 mg, 0.32 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6i (D-528) (60 mg, 70%) as a colorless syrup.

$^1$H NMR (400 MHz, CDCl$_3$): δ 7.17 (dd, J=7.9, 5.6 Hz, 2H), 7.06 (dd, J=8.2, 5.9 Hz, 2H), 6.78-6.91 (m, 4H), 6.65-6.73 (m, 2H), 5.57-6.63 (m, 1H), 4.24-4.36 (m, 1H), 3.72-3.89 (m, 6H), 3.60-3.71 (m, 2H), 3.48 (d, J=12.6 Hz, 1H), 2.36 (s, 1H), 1.40-1.54 (m, 1H), 1.26-1.37 (m, 1H).
$^{13}$C NMR (100 MHz, CDCl$_3$): δ 162.6, 162.5, 160.1, 146.4, 145.8, 137.6, 137.4, 129.8, 129.7, 129.6, 129.5, 119.5, 115.2, 115.0, 114.8, 114.7, 111.0, 73.5, 65.8, 64.0, 55.7, 54.8, 50.3, 32.7.
[α]$^{25}_D$=(−)19.4°, c=1 in MeOH. The product was converted into the corresponding hydrochloride salt; mp: 170-175° C. Anal. Calcd for [C$_{26}$H$_{27}$F$_2$NO$_4$.HCl.H$_2$O] C, H, N.

Synthesis of (2S,4R,5R)-2-(bis(4-fluorophenyl)methyl)-5-((4-nitrobenzyl)amino)tetrahydro-2H-pyran-4-ol 6j Amine 5 (126 mg, 0.40 mmol) was reacted with 4-nitrobenzaldehyde (37 mg, 0.40 mmol), glacial acetic acid (25 µL, 0.41 mmol), and Na(OAc)$_3$BH (125 mg, 0.59 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6j (140 mg, 78%) as a light yellow syrup.

$^1$H NMR (400 MHz, CDCl$_3$): δ 8.16 (d, 2H, J=8.5 Hz), 7.49 (d, 2H, J=8.5 Hz), 7.22-7.31 (m, 2H), 7.10-7.19 (m, 2H), 6.89-7.03 (m, 4H), 4.34-4.46 (m, 1H), 3.76-4.06 (m, 6H), 2.41 (s, 1H), 1.66-1.76 (m, 1H), 1.38-1.48 (m, 1H).
$^{13}$C NMR (100 MHz, CDCl$_3$): δ 160.3, 160.2, 148.1, 137.6, 137.3, 129.9, 129.8, 129.7, 129.6, 128.5, 123.6, 115.6, 115.4, 115.3, 115.1, 73.5, 67.3, 64.9, 56.5, 55.2, 50.7, 33.3.

Synthesis of (2S,4R,5R)-5-((4-aminobenzyl)amino)-2-(bis(4-fluorophenyl)methyl) tetrahydro-2H-pyran-4-ol 6k (D-529)

Compound 6j (140 mg, 0.31 mmol) was dissolved in methanol (19 mL) and Pd/C (19 mg). The mixture was then stirred at room temperature under 1 atm pressure of hydrogen for 1 h. The residue was purified by gradient silica gel column chromatography using a mixture of dichloromethane and methanol (100:1 to 6:1) to afford corresponding compound 6k (75 mg, 58%) as a yellow syrup.

$^1$H NMR (400 MHz, CDCl$_3$): δ 7.22-7.34 (m, 2H), 7.04-7.21 (m, 4H), 6.76-7.03 (m, 4H), 6.59 (d, 2H, J=7.92 Hz), 4.31-4.49 (m, 1H), 4.01-4.21 (m, 2H), 3.78-3.95 (m, 3H), 3.64-3.78 (d, J=12.9 Hz, 1H), 2.66 (s, 1H), 1.66-1.86 (m, 1H), 1.34-1.51 (m, 1H).
$^{13}$C NMR (100 MHz, CDCl$_3$): δ 161.7, 161.6 160.2, 146.4, 137.5, 137.4, 130.1, 129.8, 129.7, 129.6, 115.6, 115.4, 115.3, 115.2, 115.1, 74.0, 65.4, 62.9, 56.5, 53.9, 50.1, 32.9.
[α]$^{25}_D$=(−)34.7°, c=1 in MeOH. The product was converted into the corresponding hydrochloride salt; mp: 185-192° C. Anal. Calcd for [C$_{25}$H$_{26}$F$_2$N$_2$O$_2$.2HCl.Et$_2$O] C, H, N.

Synthesis of N-(4-((((3R,4R,6S)-6-(bis(4-fluorophenyl)methyl)-4-hydroxytetrahydro-2H-pyran-3-yl)amino)methyl)phenyl)acetamide 6l Amine 5 (60 mg, 0.19 mmol) was reacted with N-(4-formylphenyl)acetamide (37 mg, 0.23 mmol), glacial acetic acid (17 µL, 0.28 mmol), and NaCNBH₃ (21 mg, 0.32 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 61 (64 mg, 73%) as a colorless syrup. ¹H NMR (500 MHz, CDCl₃): δ 7.91 (s, 1H), 7.38 (d, J=Hz, 2H), 7.05-7.31 (m, 6H), 6.84-7.01 (m, 4H), 4.32-4.45 (m, 1H), 3.61-4.08 (m, 6H), 2.48 (s, 1H), 2.08 (s, 3H), 1.61-1.71 (m, 1H), 1.36-1.44 (m, 1H). ¹³C NMR (125 MHz, CDCl₃): δ 169.0, 162.4, 162.3, 160.5, 160.4, 137.5, 137.4, 137.1, 134.1, 129.8, 129.7, 129.6, 129.0, 127.7, 120.3, 115.5, 115.4, 115.3, 115.1, 73.7, 66.1, 63.9, 55.9, 54.8, 50.1, 32.9, 24.3. [α]²⁵_D=(−)47.4°, c=1 in CH₂Cl₂.

16. (2S,4R,5R)-2-(bis(4-fluorophenyl)methyl)-5-((4-(ethylamino)benzyl)amino) tetrahydro-2H-pyran-4-ol

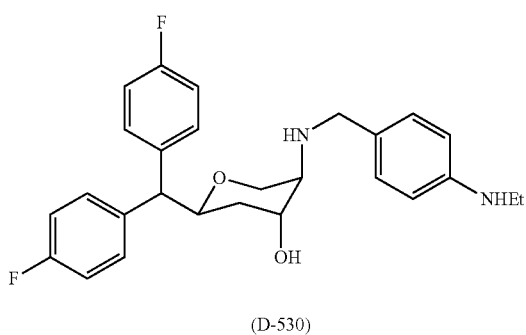

(D-530)

Amide 61 (63 mg, 0.16 mmol) was dissolved in anhydrous THF (5 mL) under a continuous flow of N₂ and the colution was cooled to 0° C. Then LiAlH₄ (10 mg, 0.20 mmol) was added in portions and the reaction mixture was allowed to reach room temperature slowly and stirred for 24 h. Next, the reaction was quenched by slow addition of methanol followed by a solution of saturated NH₄Cl at 0° C. The product was extracted with ethyl acetate and concentrated on a rotary evaporator. The residue was purified by gradient silica gel column chromatography using a mixture of dichloromethane and methanol (100:1 to 6:1) to afford corresponding compound 6m (D-530) (52 mg, 85%) as a colorless semi solid. ¹H NMR (500 MHz, CDCl₃): δ 7.21-7.34 (m, 2H), 7.10-7.20 (m, 2H), 7.08 (d, J=8.2 Hz, 2H), 6.87-7.02 (m, 4H), 6.54 (d, J=8.2 Hz, 2H), 4.33-4.42 (m, 1H), 3.83-3.98 (m, 3H), 3.69-3.80 (m, 2H), 3.59 (d, J=12.8 Hz, 1H), 3.13 (dd, J=7.0, 7.3 Hz, 2H), 2.43 (s, 1H), 1.61-1.74 (m, 1H), 1.33-1.45 (m, 1H), 1.24 (t, J=7.3 Hz, 3H). ¹³C NMR (125 MHz, CDCl₃): δ 162.5, 162.4, 160.5, 160.4, 147.6, 137.8, 137.5, 129.9, 129.8, 129.7, 129.6, 129.2, 128.4, 115.5, 115.3, 115.2, 115.1, 112.7, 73.5, 67.2, 64.8, 56.2, 54.8, 50.9, 38.5, 33.1, 14.8. [α]²⁵_D=(−) 62.4°, c=1 in CH₂Cl₂. The product was converted into the corresponding hydrochloride salt; mp: 203-210° C. Anal. Calcd for [C₂₇H₃₀F₂N₂O₂.2HCl] C, H, N.

Synthesis of (2S,4R,5R)-2-(bis(4-fluorophenyl)methyl)-5-((3-fluoro-4-hydroxybenzyl)amino) tetrahydro-2H-pyran-4-ol

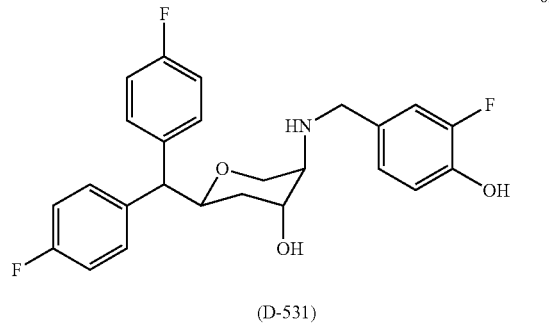

(D-531)

Amine 5 (50 mg, 0.16 mmol) was reacted with 3-fluoro-4-hydroxybenzaldehyde (29 mg, 0.20 mmol), glacial acetic acid (16 µL, 0.27 mmol), and NaCNBH₃ (17 mg, 0.27 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6n (D-531) (50 mg, 80%) as a colorless semi solid. ¹H NMR (500 MHz, CDCl₃): δ 7.22-7.32 (m, 2H), 7.09-7.18 (m, 2H), 6.84-7.02 (m, 5H), 6.80 (d, J=7.9 Hz, 1H), 6.68 (t, J=8.5 Hz, 1H), 5.0 (br s, 1H), 4.43 (t, J=9.6 Hz, 1H), 4.11 (s, 1H), 3.98 (d, J=11.3 Hz, 1H), 3.93 (d, J=8.9 Hz, 1H), 3.87 (d, J=12.2 Hz, 1H), 3.81 (d, J=12.5 Hz, 1H), 3.63 (d, J=12.5 Hz, 1H), 2.62 (s, 1H), 1.62-1.80 (m, 1H), 1.44 (d, J=14.3 Hz, 1H). ¹³C NMR (125 MHz, CDCl₃): δ 162.6, 162.5, 160.5, 160.4, 152.3, 150.4, 143.8, 143.7, 137.4, 137.3, 129.9, 129.8, 129.7, 129.6, 128.8, 124.9, 118.2, 116.1, 115.9, 115.6, 115.4, 115.3, 115.2, 73.8, 65.9, 63.3, 56.2, 54.8, 49.9, 32.9. [α]²⁵_D=(−)41.0°, c=1 in MeOH. The product was converted into the corresponding hydrochloride salt; mp: 150-155° C. Anal. Calcd for [C₂₅H₂₄F₃NO₃.HCl.Et₂O] C, H, N.

Synthesis of (2S,4R,5R)-2-(bis(4-fluorophenyl)methyl)-5-((4-(dimethylamino)benzyl)amino)tetrahydro-2H-pyran-4-ol

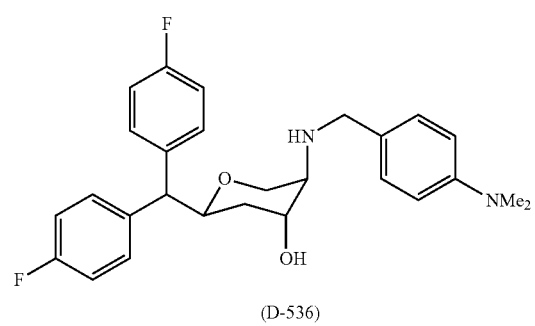

(D-536)

Amine 5 (40 mg, 0.13 mmol) was reacted with 4-(dimethylamino)benzaldehyde (23 mg, 0.15 mmol), glacial acetic acid (16 μL, 0.27 mmol), and NaCNBH₃ (14 mg, 0.23 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6o (D-536) (50 mg, 88%) as a colorless semi solid. ¹H NMR (500 MHz, CDCl₃): δ 7.22-7.32 (m, 2H), 7.08-7.20 (m, 4H), 6.88-7.02 (m, 4H), 6.68 (d, J=8.5 Hz, 2H), 4.32-4.44 (m, 1H), 3.84-4.03 (m, 3H), 3.78 (d, J=12.5 Hz, 3.64 (d, J=12.8 Hz, 1H), 2.92 (s, 6H), 2.46 (s, 1H), 1.63-1.74 (m, 1H), 1.35-1.45 (m, 1H). ¹³C NMR (125 MHz, CDCl₃): δ 162.4, 162.3, 160.5, 160.4, 149.9, 137.7, 137.5, 129.9, 129.8, 129.7, 129.6, 129.1, 115.5, 115.3, 115.2, 115.1, 112.6, 73.5, 67.0, 64.5, 56.2, 54.7, 53.4, 50.8, 50.6, 40.7, 33.1, 29.7. [α]$^{25}_D$=(−)19.3°, c=1 in CH₂Cl₂. The product was converted into the corresponding hydrochloride salt; mp: 190-195° C. Anal. Calcd for [C₂₇H₃₀F₂N₂O₂.2HCl.Et₂O] C, H, N.

Synthesis of (2S,4R,5R)-2-(bis(4-fluorophenyl) methyl)-5-(((6-methoxypyridin-3-yl)methyl)amino) tetrahydro-2H-pyran-4-ol

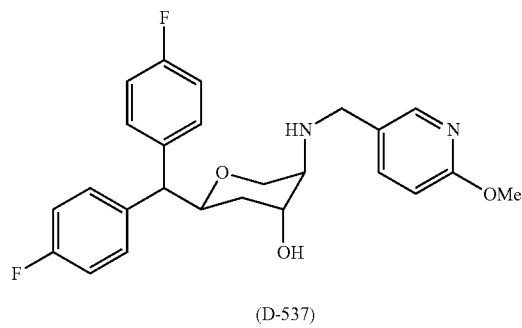

(D-537)

Amine 5 (60 mg, 0.19 mmol) was reacted with 6-methoxynicotinaldehyde (31 mg, 0.23 mmol), glacial acetic acid (13 μL, 0.22 mmol), and NaCNBH₃ (22 mg, 0.34 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6p (D-537) (60 mg, 72%) as a colorless syrup. ¹H NMR (500 MHz, CDCl₃): δ 8.03 (d, J=2.1 Hz, 1H), 7.55 (dd, J=2.4, 8.6 Hz, 1H), 7.23-7.31 (m, 2H), 7.09-7.18 (m, 2H), 6.88-7.02 (m, 4H), 6.70 (d, J=8.2 Hz, 1H), 4.34-4.43 (m, 1H), 3.85-3.99 (m, 6H), 3.75-3.83 (m, 2H), 3.64 (d, J=13.1 Hz, 1H), 2.42 (s, 1H), 2.10 (br s, 1H), 1.62-1.73 (m, 1H), 1.35-1.45 (m, 1H). ¹³C NMR (125 MHz, CDCl₃): δ 163.54, 162.5, 162.4, 160.5, 160.4, 146.1, 139.0, 137.6, 137.4, 129.9, 129.8, 129.7, 129.6, 127.9, 115.6, 115.4, 115.3, 115.1, 110.7, 73.5, 67.1, 64.7, 56.1, 55.0, 53.4, 48.0, 33.2. [α]$^{25}_D$=(−)42.5.0°, c=1 in CH₂Cl₂. The product was converted into the corresponding hydrochloride salt; mp: 180-185° C. Anal. Calcd for [C₂₅H₂₆F₂N₂O₃.2HCl] C, H, N.

Synthesis of tert-butyl (4-formylphenyl)(methyl)carbamate

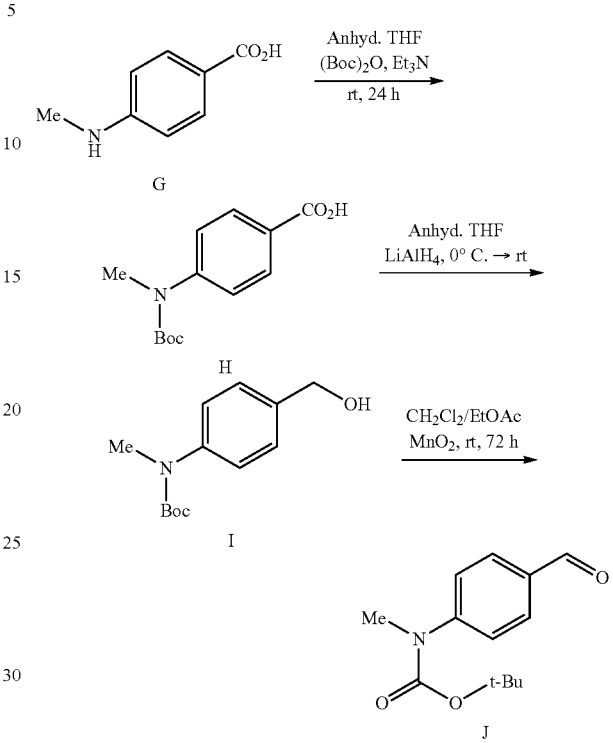

Amine G (1.0 g, 6.62 mmol) was dissolved in anhydrous THF (6 mL) and then Et₃N (1.76 mL, 13.23 mmol) was added, followed by (Boc)₂O (1.96 g, 9.00 mmol). The resulting mixture was stirred at room temperature for 24 h. The reaction was then quenched by the addition of 1N HCl and extracted several times with ethyl acetate. The organic layer was dried over Na₂SO₄ and concentrated under vacuum. The crude product H was purified by gradient column chromatography using dichloromethane and methanol (100:1 to 10:1) to obtain the desired product H as light brown syrup (0.54 g). ¹H NMR (400 MHz, CDCl₃): δ 7.99 (d, J=8.6 Hz, 2H), 6.55 (d, J=8.6 Hz, 2H), 2.99 (s, 3H, 1.55 (s, 9H). ¹³C NMR (100 MHz, CDCl₃): δ 161.8, 154.0, 148.0, 132.7, 115.0, 111.1, 84.7, 29.9, 27.4.

Boc protected acid was dissolved in anhydrous THF (8 mL) and cooled to 0° C. Then LiAlH₄ (0.122 g, 3.23 mmol) was added in portions and the reaction was allowed to stir at room temperature overnight. The reaction mixture was then cooled to 0° C. and quenched with slow addition of methanol (5 mL) followed by saturated NH₄Cl (5 mL). The mixture was then repeatedly extracted with ethyl acetate (10 mL×3). The organic layer was dried on Na₂SO₄ and concentrated under reduced pressure on a rotary evaporator. The crude product was purified via gradient column chromatography using dichloromethane and methanol (100:1 to 10:1) to afford the desired product I as white solid. ¹H NMR (500 MHz, CDCl₃): δ 7.30 (d, J=8.2 Hz, 2H), 7.20 (d, J=8.2 Hz, 2H), 4.64 (s, 2H), 3.24 (s, 3H), 1.44 (s, 9H). ¹³C NMR (125 MHz, CDCl₃): δ 154.8, 143.0, 138.0, 132.1, 127.2, 125.5, 80.3, 64.6, 28.3.

The alcohol I (0.16 g, 0.67 mmol) was treated with MnO₂ (0.23 g, 2.70 mmol) in dichloromethane (5 mL) and stirred at room temperature for 72 h. The reaction mixture was then filtered through a pad of celite and concentrated under reduced pressure on a rotary evaporator. The crude product J was sufficient pure and used directly in following step without further purification. $^1$H NMR (500 MHz, CDCl$_3$): δ 9.95 (s, 1H), 7.83 (d, J=8.6 Hz, 2H), 7.49 (d, J=8.6 Hz, 2H), 3.31 (s, 3H), 1.49 (s, 9H). $^{13}$C NMR (125 MHz, CDCl$_3$): δ 191.2, 153.9, 149.2, 132.6, 130.1, 124.6, 81.4, 36.8, 28.2.

Synthesis of (4-((((3R,4R,6S)-6-(bis(4-fluorophenyl)methyl)-4-hydroxytetrahydro-2H-pyran-3-yl)amino)methyl)phenyl)(methyl)carbamate

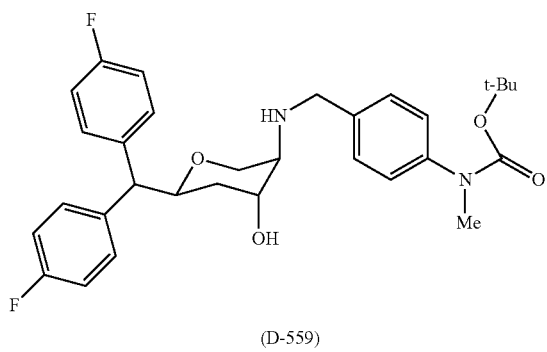

(D-559)

Amine 5 (60 mg, 0.19 mmol) was reacted with tert-butyl (4-formylphenyl)carbamate (49 mg, 0.21 mmol), glacial acetic acid (13 μL, 0.22 mmol), and Na(OAc)$_3$BH (68 mg, 0.32 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6q (D-559) as colorless syrup (60 mg, 59%) as a white solid. $^1$H NMR (500 MHz, CDCl$_3$): δ 7.24-7.31 (m, 2H), 7.11-7.19 (m, 2H), 6.88-7.01 (m, 4H), 4.35-4.45 (m, 1H), 3.98-4.05 (m, 1H), 3.84-3.98 (m, 3H), 3.81 (d, J=11.9 Hz, 1H), 3.73 (d. J=13.4 Hz, 1H), 3.22 (s. 3H), 2.50 (br s, 1H), 1.66-1.77 (m, 1H), 1.36-1.53 (m, 10H). $^{13}$C NMR (125 MHz, CDCl$_3$): δ 162.5, 162.4, 160.6, 160.5, 154.8, 143.0, 137.7, 137.5, 129.9, 129.8, 129.7, 129.6, 128.6, 125.5, 115.6, 115.4, 115.3, 115.2, 80.4, 73.6, 65.9, 56.4, 54.7, 50.6, 37.4, 33.1, 28.4, 15.3. [α]$^{25}_D$=(−)51.4°, c=1 in CH$_2$Cl$_2$. The product was converted into the corresponding hydrochloride salt; mp: 184-190° C. Anal. Calcd for [C$_{31}$H$_{36}$F$_2$N$_2$O$_4$·2HCl] C, H, N.

Synthesis of Benzotriazole-5-carbaldehyde

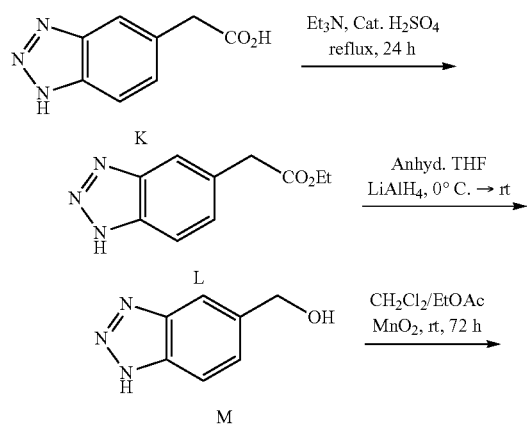

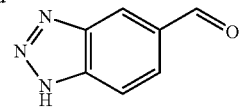

The acid K (5 g, 30.65 mmol) was dissolved in EtOH (50 mL) and concentrated H$_2$SO$_4$ (1.92 mL) was added. The mixture was then refluxed for 24 h., cooled to room temperature and neutralized of saturated NaHCO$_3$. The solution was then repeatedly extracted with ethyl acetate (20 mL×3). The organic layer was dried over Na$_2$SO$_4$ and concentrated under reduced pressure on a rotary evaporator. The crude product L was sufficiently pure and used directly in the next step without further purification. $^1$H NMR (500 MHz, CDCl$_3$): δ 8.78 (s, 1H), 8.16 (d, J=8.2 Hz, 1H), 7.95 (d, J=8.2 Hz, 1H), 4.45 (q, J=7.0 Hz, 2H), 1.43 (t, J=7.3 Hz, 3H). $^{13}$C NMR (125 MHz, CDCl$_3$): δ 166.3, 141.3, 139.5, 128.0, 127.4, 119.1, 113.7, 61.7, 14.3.

The ester L (3.4 g, 17.78 mmol) was dissolved in anhydrous THF (38 mL) and cooled to 0° C. Then, LiALH$_4$ (1.0 g, 26.67 mmol) was added in portions and the mixture was allowed to stir at room temperature for 24 h. The reaction mixture was then cooled to 0° C. and quenched with slow addition of methanol (10 mL) followed by saturated NH$_4$Cl (10 mL). The mixture was then repeatedly extracted with ethyl acetate (10 mL×3). The organic layer was dried on Na$_2$SO$_4$ and concentrated under reduced pressure on a rotary evaporator. The crude product was purified via gradient column chromatography using dichloromethane and methanol (100:1 to 10:1) to afford the desired product M as yellow solid. $^1$H NMR (500 MHz, CDCl$_3$): δ 7.81 (s, 1H), 7.80 (d, J=8.9 Hz, 1H), 7.39 (d, J=8.6 Hz, 1H), 4.78 (s, 2H). $^{13}$C NMR (125 MHz, CDCl$_3$): δ 139.9, 138.6, 137.9, 125.1, 114.9, 111.3, 63.9.

The alcohol M (2.0 g, 13.41 mmol) was treated with MnO$_2$ (4.66 g, 53.64 mmol) in a mixture of dichloromethane (60 mL) and ethyl acetate (40 mL). The solution was then stirred at room temperature for 72 h. The reaction mixture was then filtered through a pad of celite and concentrated under reduced pressure on a rotary evaporator. The crude product N was sufficient pure and used directly in following step without further purification. $^1$H NMR (400 MHz, CDCl$_3$): δ 9.99 (s, 1H), 8.33 (s, 1H), 7.83 (d, J=8.2 Hz, 1H), 7.73 (d, J=8.2 Hz, 1H). $^{13}$C NMR (125 MHz, CDCl$_3$): δ 191.8, 140.9, 139.5, 133.4, 124.9, 121.8, 113.9.

Synthesis of (2S,4R,5R)-5-(((1H-benzo[d][1,2,3]triazol-5-yl)methyl)amino)-2-(bis(4-fluorophenyl)methyl)tetrahydro-2H-pyran-4-ol

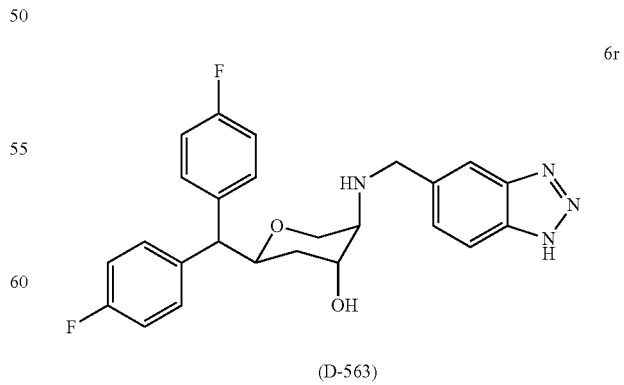

(D-563)

Amine 5 (60 mg, 0.19 mmol) was reacted with benzotriazole-5-carbaldehyde (31 mg, 0.21 mmol), glacial acetic acid (13 μL, 0.22 mmol), and Na(OAc)$_3$BH (68 mg, 0.32 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6r (D-563) as colorless syrup (40 mg, 47%) as a white solid. $^1$H NMR (500 MHz, CDCl$_3$): δ 7.77 (s, 1H), 7.71 (d, J=8.6 Hz, 1H), 7.32 (d, J=8.2 Hz, 1H), 7.21 (dd, J=5.5, 8.6 Hz, 2H), 7.10 (dd, J=5.5, 8.6 Hz, 2H), 6.78-6.98 (m, 4H), 4.32-4.46 (m, 1H), 4.03-4.15 (m, 2H), 3.91-4.03 (m, 3H), 3.89 (d, J=9.2 Hz, 1H), 3.81 (d, J=12.2 Hz, 1H), 3.55 (br s, 1H), 2.67 (br s, 1H), 1.60-1.73 (m, 1H), 1.36-1.49 (m, 1H). $^{13}$C NMR (125 MHz, CDCl$_3$): δ 162.4, 162.3, 160.5, 160.4, 137.4, 137.3, 134.0, 129.7, 129.6, 126.7, 115.4, 115.3, 115.2, 115.0, 114.5, 73.9, 64.7, 63.3, 56.0, 54.8, 50.2, 32.6. $[α]^{25}_D$=(−)51.3°, c=1 in MeOH. The product was converted into the corresponding hydrochloride salt; mp: 220-230° C. Anal. Calcd for [C$_{25}$H$_{24}$F$_2$N$_4$O$_2$.2HCl] C, H, N.

Synthesis of (2S,4R,5R)-2-(bis(4-fluorophenyl)methyl)-5-((2-hydroxy-4-methoxybenzyl)amino)tetrahydro-2H-pyran-4-ol

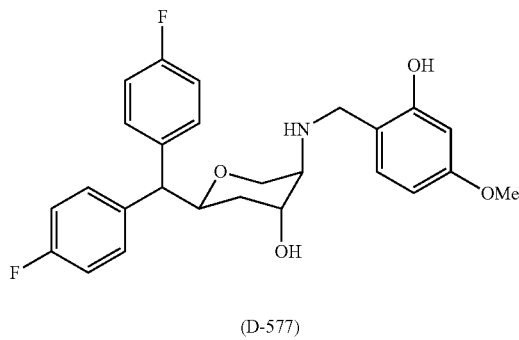

(D-577)

6s

Amine 5 (60 mg, 0.19 mmol) was reacted with 2-hydroxy-4-methoxybenzaldehyde (34 mg, 0.21 mmol), glacial acetic acid (13 μL, 0.22 mmol), and Na(OAc)$_3$BH (68 mg, 0.32 mmol) in a mixture of 1,2-dichloroethane (3 mL) and methanol (1 mL). The residue was purified by gradient silica gel column chromatography using a mixture of dichloromethane and methanol (100:1 to 6:1) to afford corresponding compound 6s (D-577) as colorless syrup (50 mg, 58%) as a white solid. $^1$H NMR (500 MHz, CDCl$_3$): δ 7.26 (dd, J=8.5, 5.5 Hz, 2H), 7.15 (dd, J=8.5, 5.2 Hz, 2H), 6.89-7.04 (m, 4H), 6.83 (d, J=8.2 Hz, 1H), 6.37-6.44 (m, 1H), 6.33 (dd, J=8.2, 2.5 Hz, 1H), 4.33-4.45 (m, 1H), 4.06 (d, J=13.7 Hz, 1H), 4.02 (d, J=2.1 Hz, 1H), 3.94 (dd, J=11.9, 1.2 Hz, 1H), 3.73-3.90 (m, 3H), 3.77 (s, 3H), 2.50 (s, 1H), 1.53-1.65 (m, 1H), 1.40-1.52 (m, 1H). $^{13}$C NMR (125 MHz, CDCl$_3$): δ 162.6, 162.5, 160.6, 160.5, 159.1, 137.3, 129.8, 129.7, 129.7, 129.7, 129.1, 115.6, 115.5, 115.4, 115.2, 114.2, 105.1, 102.1, 73.6, 66.6, 64.0, 55.6, 55.2, 55.0, 49.6, 33.4. $[α]^{25}_D$=(−)53.3°, c=1 in MeOH. The product was converted into the corresponding hydrochloride salt; mp: 170-175° C. Anal. Calcd for [C$_{26}$H$_{27}$F$_2$NO$_4$.HCl] C, H, N.

Synthesis of Synthesis of 2-aminobenzo[d]thiazole-6-carbaldehyde

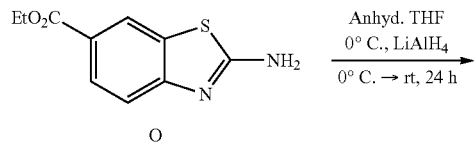

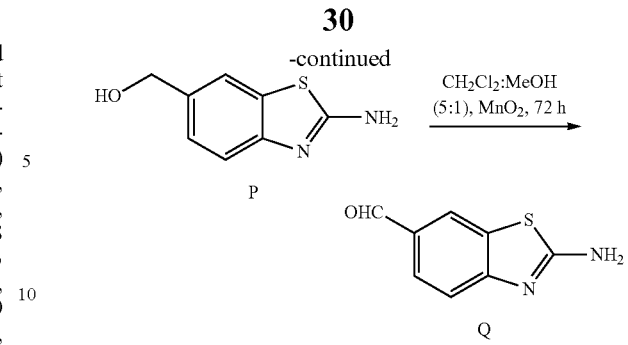

The ester (1.0 g, 4.5 mmol) was dissolved in anhydrous THF and the RB flask was cooled to 0° C. Then LiAlH$_4$ was added slowly and the flask was stirred at 0° C. for additional 10 min. The flask was then stirred at room temperature for 24 h. The reaction was then cooled, quenched with methanol, NH$_4$Cl Rochelle's salt and diluted with ethyl acetate (10 mL). The organic layer was separated and the aqueous layer was extracted with additional ethyl acetate (3×10 mL). The organic layers were combined, dried over Na$_2$SO$_4$ and concentrated under vacuo on a rotary evaporator to obtain a yellow solid. The crude product was purified via gradient silica gel column chromatography using a mixture of CH$_2$Cl$_2$ and methanol (100:1 to 5:1) to obtain the desired alcohol as yellow solid (420 mg, 52%). The alcohol (420 mg, 2.33 mmol) was dissolved in a mixture of CH$_2$Cl$_2$ and methanol (5:1) and MnO$_2$ (81 mg, 9.32 mmol). The mixture was then stirred at room temperature for 48 h following which additional amount of MnO$_2$ (40 mg) was added after TLC showed incompletion of the reaction. The mixture was stirred for additional 24 h and then filtered through a whatman filter paper (grade 8) and the filtrate was concentrated under vacuo on a rotary evaporator to obtain the desired aldehyde as a yellow solid (400 mg, 95%). $^1$H NMR (500 MHz, CDCl$_3$): δ 7.57 (d, J=0.9 Hz, 1H), 7.35-7.46 (m, 1H), 7.25 (dd, J=8.2, 1.8 Hz, 1H), 6.45 (br s, 1H), 4.53 (s, 2H), 4.0 (br s, 1H). $^{13}$C NMR (125 MHz, CDCl$_3$): δ 167.6, 150.5, 134.9, 130.6, 125.1, 119.4, 117.7, 64.2. 2-aminobenzo[d]thiazole-6-carbaldehyde: $^1$H NMR (500 MHz, CDCl$_3$): δ 9.81 (s, 1H), 8.01 (d, J=1.5 Hz, 1H), 7.70 (dd, J=8.2, 1.5 Hz, 1H), 7.42 (d, J=8.5 Hz, 1H), 3.70 (br s, 1H). $^{13}$C NMR (125 MHz, CDCl$_3$): δ 191.3, 164.5, 157.1, 130.3, 128.7, 122.6, 118.0.

Synthesis of (2S,4R,5R)-5-(((2-aminobenzo[d]thiazol-6-yl)methyl)amino)-2-(bis(4-fluorophenyl)methyl)tetrahydro-2H-pyran-4-ol

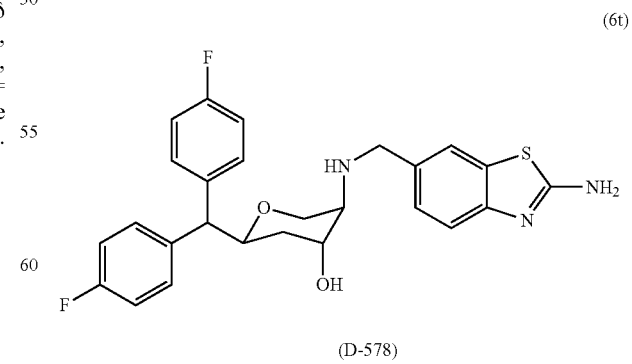

(D-578)

(6t)

Amine 5 (60 mg, 0.19 mmol) was reacted with 2-aminobenzo[d]thiazole-6-carbaldehyde (37 mg, 0.21 mmol), glacial acetic acid (16 μL, 0.22 mmol), and Na(OAc)$_3$BH (113 mg, 0.38 mmol) in a mixture of 1,2-dichloroethane (4.5 mL) and methanol (1.5 mL). The residue was purified by gradient silica gel column chromatography using a mixture of dichloromethane and methanol (100:1 to 6:1) to afford corresponding compound 6t (D-578) as light yellow solid syrup (45 mg, 50%). $^1$H NMR (500 MHz, CDCl$_3$): δ 7.54 (s, 1H), 7.30 (d, J=8.2 Hz, 1H), 7.20 (dd, J=8.5, 6.1 Hz, 2H), 7.16 (dd, J=8.2, 1.1 Hz, 1H), 7.09 (dd, J=8.6, 5.5 Hz, 2H), 6.79-6.96 (m, 4H), 4.38 (dt, J=10.1, 2.4 Hz, 1H), 4.06 (s, 1H), 3.98 (d, J=13.1 Hz, 1H), 3.92 (dd, J=12.8, 1.5 Hz, 1H), 3.82-3.92 (m, 1H), 3.79 (d, J=12.5 Hz, 1H), 3.34 (br s, 2H), 2.64 (br s, 1H), 1.56-1.71 (m, 1H), 1.35-1.47 (m, 1H). $^{13}$C NMR (125 MHz, CDCl$_3$): δ 168.0, 162.4, 162.3, 160.5, 160.4, 151.4, 137.4, 137.2, 131.3, 129.7, 129.6, 126.9, 121.3, 118.2, 115.4, 115.3, 115.2, 115.0, 73.9, 64.5, 62.9, 55.8, 54.7, 50.2, 32.6. $[α]^{25}_D$= (−)30.6°, c=1 in MeOH. The product was converted into the corresponding hydrochloride salt; mp: 210-215° C. Anal. Calcd for [C$_{26}$H$_{25}$F$_2$N$_3$O$_2$S.3HCl.3H$_2$O] C, H, N.

Synthesis of 2-oxo-2,3-dihydrobenzo[d]oxazole-6-carbaldehyde

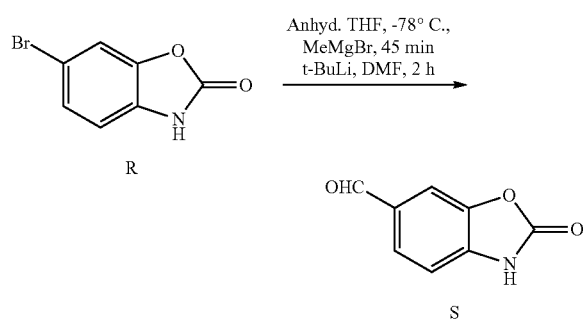

The bromo compound R (1.0 g, 4.67 mmol) was taken in an oven-dried RB equipped with magnetic stir-bar and dissolved in anhydrous THF (9 mL). The solution was cooled to −78° C. and MeMgBr (1.8 mL) was added slowly. The mixture was stirred for 45 min and anhydrous THF (37.5 mL) was added slowly to maintain the internal temperature at −50° C. After the solution was cooled back to −78° C., t-BuLi (10.6 mL, 9.8 mmol, 1.6 M in pentane) was added dropwise. Next, DMF (2.2 mL, 28.1 mmol) was added slowly to the yellow solution and the dry-ice bath was removed after 15 min. After 2 h, the reaction was quenched with water and the THF was removed under vacuo on a rotary evaporator. The residue was dissolved in ethyl acetate and washed with 1N HCl (5 mL). The organic layer was separated and the aqueous layer was extracted with ethyl acetate (3×5 mL). The organic layers were combined, dried over Na$_2$SO$_4$ and concentrated under vacuo on a rotary evaporator. The crude was first recrystallized from hexanes/ethyl acetate and then purified via gradient silica gel column chromatography using a mixture of hexanes and ethyl acetate (10:1 to 1:1) to obtain the desired aldehyde S as a white solid (500 mg, 66%). $^1$H NMR (500 MHz, CDCl$_3$): δ 9.85 (s, 1H), 7.66 (dd, J=7.9 Hz, 1.2 Hz, 1H), 7.63 (s, 1H), 7.11 (d, J=7.9 Hz, 1H). $^{13}$C NMR (125 MHz, CDCl$_3$): δ 190.9, 155.2, 144.1, 135.9, 131.4, 128.2, 109.6, 109.5.

Synthesis of 6-((((3R,4R,6S)-6-(bis(4-fluorophenyl)methyl)-4-hydroxytetrahydro-2H-pyran-3-yl)amino)methyl)benzo[d]oxazol-2(3H)-one

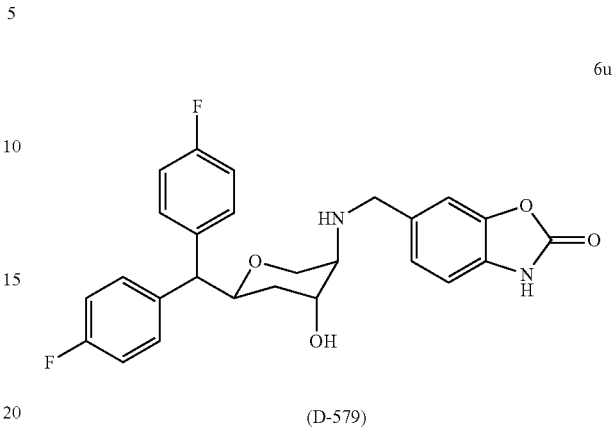

(D-579)

Amine 5 (60 mg, 0.19 mmol) was reacted with 2-oxo-2,3-dihydrobenzo[d]oxazole-6-carbaldehyde (34 mg, 0.21 mmol), glacial acetic acid (13 μL, 0.22 mmol), and Na(OAc)$_3$BH (113 mg, 0.38 mmol) in a mixture of 1,2-dichloroethane (3 mL) and methanol (1 mL). The residue was purified by gradient silica gel column chromatography using a mixture of dichloromethane and methanol (100:1 to 6:1) to afford corresponding compound 6u (D-579) as colorless syrup (40 mg, 46%) as a yellowish solid. $^1$H NMR (500 MHz, CDCl$_3$): δ 7.26 (dd, J=8.5, 5.5 Hz, 2H), 7.18 (s, 1H), 7.13 (dd, J=8.5, 5.5 Hz, 2H), 7.06 (d. J=7.9 Hz, 1H), 6.97 (t, J=8.9 Hz, 2H), 6.91 (t, J=8.9 Hz, 2H), 6.81 (d, J=7.9 Hz, 1H), 4.44 (m, 1H), 4.11-4.19 (m, 1H), 4.02 (d, J=11.6 Hz, 1H), 3.91-3.99 (m, 2H), 3.88 (d, J=14.9 Hz, 1H), 3.82 (d, J=13.1 Hz, 1H), 2.70 (s, 1H), 2.02 (br s, 1H), 1.70-1.85 (m, 1H), 1.39-1.52 (m, 1H). $^{13}$C NMR (125 MHz, CDCl$_3$): δ 162.5, 162.4, 160.5, 160.4, 156.0, 143.8, 137.4, 129.8, 129.7, 129.7, 129.4, 124.8, 115.6, 115.4, 115.3, 115.2, 110.4, 109.6, 73.9, 65.9, 63.6, 56.4, 54.9, 50.6, 32.9. $[α]^{25}_D$=(−)58.0°, c=1 in CH$_2$Cl$_2$. The product was converted into the corresponding hydrochloride salt; mp: 170-175° C. Anal. Calcd for [C$_{26}$H$_{24}$F$_2$N$_2$O$_4$.HCl.H$_2$O] C, H, N.

5-methoxynicotinaldehyde

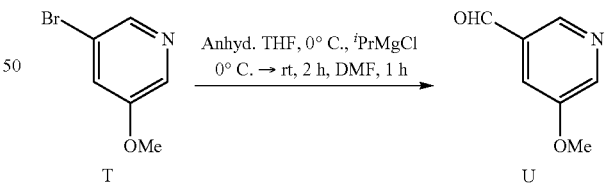

The bromo compound T (100 mg, 0.53 mmol) was taken in an oven-dried RB equipped with magnetic stir-bar and dissolved in anhydrous THF (1 mL). Then, $^i$PrMgCl (0.3 mL) was added at 0° C. and the resulting mixture was stirred at room temperature for 2 h (the solution turned into light brown beer color). Next, DMF (0.1 mL) in anhydrous THF (0.1 mL) was added slowly. Initially formed solid was slowly dissolved and the solution color turned from light brown to light yellow. After 1 h, the reaction was cooled to 0° C. and quenched with water (2 mL). The organic layer was separated and the aqueous layer was washed with additional amount of CH$_2$Cl$_2$ (3×3 mL). The organic layers were combined, dried over Na$_2$SO$_4$ and concentrated under vacuo on a rotary evaporator. The crude product was purified via gradient silica gel column chromatography using a mixture of hexanes and ethyl acetate (20:1 to 1:1) to obtain the desired product U as a colorless syrup (45 mg, 63%). $^1$H NMR (500 MHz, CDCl$_3$): δ 10.09 (s, 1H), 8.65 (d, J=0.9 Hz, 1H), 8.54 (d, J=3.1 Hz, 1H), 7.60 (dd, J=5.1, 1.5 Hz, 1H). $^{13}$C NMR (125 MHz, CDCl$_3$): δ 190.6, 156.2, 145.1, 144.8, 132.0, 116.3, 55.7.

Synthesis of (2S,4R,5R)-2-(bis(4-fluorophenyl)methyl)-5-(((5-methoxypyridin-3-yl)methyl)amino)tetrahydro-2H-pyran-4-ol

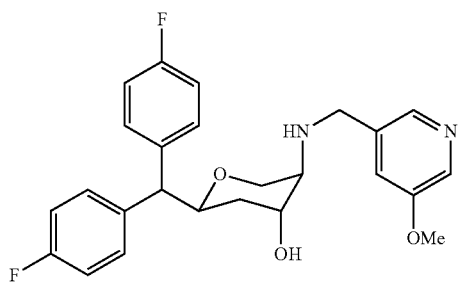

6v

Amine 5 (60 mg, 0.19 mmol) was reacted with 5-methoxynicotinaldehyde (29 mg, 0.21 mmol), glacial acetic acid (13 µL, 0.22 mmol), and Na(OAc)$_3$BH (113 mg, 0.38 mmol) in a mixture of 1,2-dichloroethane (3 mL) and methanol (1 mL). The residue was purified by gradient silica gel column chromatography using a mixture of dichloromethane and methanol (100:1 to 6:1) to afford corresponding compound 6v as colorless syrup (10 mg, 23%) as a colorless syrup. $^1$H NMR (500 MHz, CDCl$_3$): δ 8.04-8.25 (m, 2H), 7.05-7.34 (m, 4H), 6.85-7.03 (m, 4H), 4.41 (dt, J=10.1, 2.5 Hz, 1H), 4.00-4.07 (m, 1H), 3.96 (dd, J=12.2, 2.1 Hz, 1H), 3.92 (d, J=13.7 Hz, 1H), 3.85-3.91 (m, 1H), 3.80-3.85 (m, 4H), 3.78 (d, J=13.7 Hz, 1H), 2.50 (s, 1H), 2.35 (br s, 1H), 1.64-1.77 (m, 1H), 1.38-1.48 (m, 1H). $^{13}$C NMR (125 MHz, CDCl$_3$): δ 162.5, 162.4, 160.6, 160.5, 155.8, 141.5, 140.3, 137.5, 137.4, 136.9, 136.4, 129.8, 129.7, 129.6, 120.6, 119.1, 115.6, 115.4, 115.3, 115.2, 73.7, 66.6, 64.5, 56.3, 55.6, 55.1, 48.2, 33.2.

Synthesis of tert-butyl 3-((((3R,4R,6S)-6-(bis(4-fluorophenyl)methyl)-4-hydroxytetrahydro-2H-pyran-3-yl)amino)methyl)-5-methoxy-1H-indole-1-carboxylate

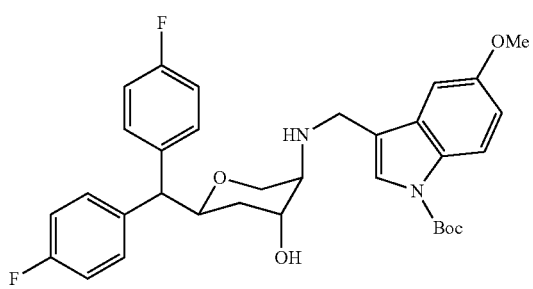

6w

Amine 5 (60 mg, 0.19 mmol) was reacted with 3-formyl-5-methoxy-1H-indole-1-carboxylate (60 mg, 0.22 mmol), glacial acetic acid (17 µL, 0.29 mmol), and Na(OAc)$_3$BH (73 mg, 0.34 mmol) in a mixture of 1,2-dichloroethane (3 mL) and methanol (1 mL). The residue was purified by gradient silica gel column chromatography using a mixture of dichloromethane and methanol (100:1 to 6:1) to afford corresponding compound 6w as colorless syrup (10 mg, 10%) as a colorless syrup.

Synthesis of 1H-benzo[d]imidazole-5-carbaldehyde

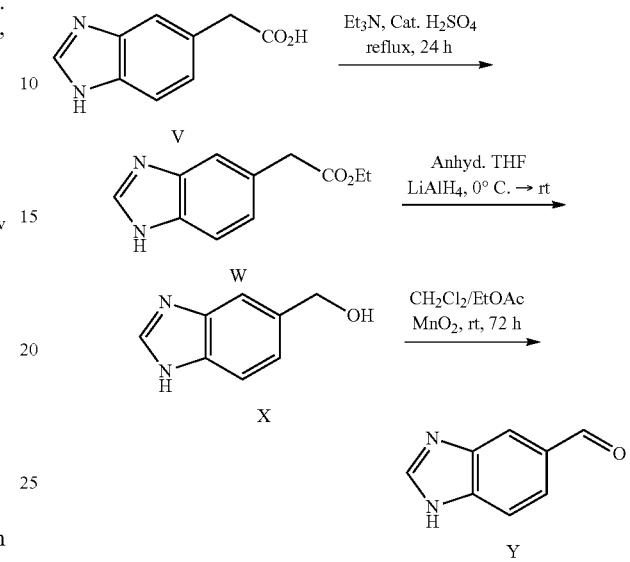

The carboxylic acid V (10.0 g, 56.8 mmol) was dissolved in ethanol (100 mL) and catalytic amount of H$_2$SO$_4$ was added. The solution was then refluxed for 24 h, cooled to room temperature and neutralized with saturated NaHCO$_3$ solution. The organic layer was separated and the aqueous layer was extracted with ethyl acetate (3×20 mL). The organic layers were combined, dried over Na$_2$SO$_4$ and concentrated under vacuo on a rotary evaporator to obtain the ester W as a yellowish solid (11.43 g, 99%). Without further purification, the ester (11.43 g, 56.0 mmol) was dissolved in anhydrous THF (100 mL) and cooled to 0° C. under a steady flow of N$_2$. Next, LiAlH$_4$ (3.4 g, 90.2 mmol) was added to the solution and stirred at room temperature for 24 h. After cooling the solution to 0° C., the reaction was quenched by the addition of methanol, NH$_4$Cl, Rochelle's salt and filtered through a whatman filter paper (grade 8). The filtrate was concentrated under vacuo on a rotary evaporator to obtain the desired product as a light brown solid (7.99 g, 96%). The alcohol (7.99 g, 53.9 mmol) was dissolved in CH$_2$Cl$_2$ (200 mL) and MnO$_2$ (19.8 g, 227.6 mmol). The mixture was then stirred at room temperature for 72 h and filtered through a whatman filter paper (grade 8). The filtrate was concentrated under vacuo on a rotary evaporator to obtain the desired aldehyde as a light brown solid (7.5 g, 95%).

Synthesis of (2S,4R,5R)-5-(((1H-benzo[d]imidazol-5-yl)methyl)amino)-2-(bis(4-fluorophenyl)methyl)tetrahydro-2H-pyran-4-ol

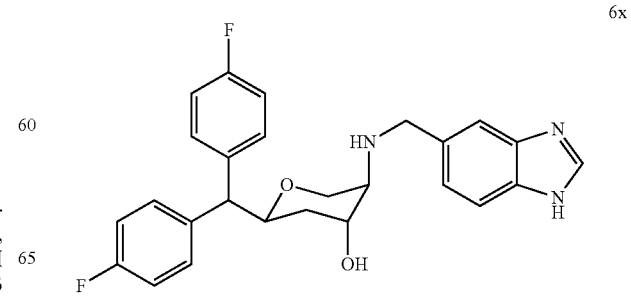

6x

Synthesis of 1-methyl-2-oxo-2,3-dihydro-1H-benzo[d]imidazole-5-carbaldehyde

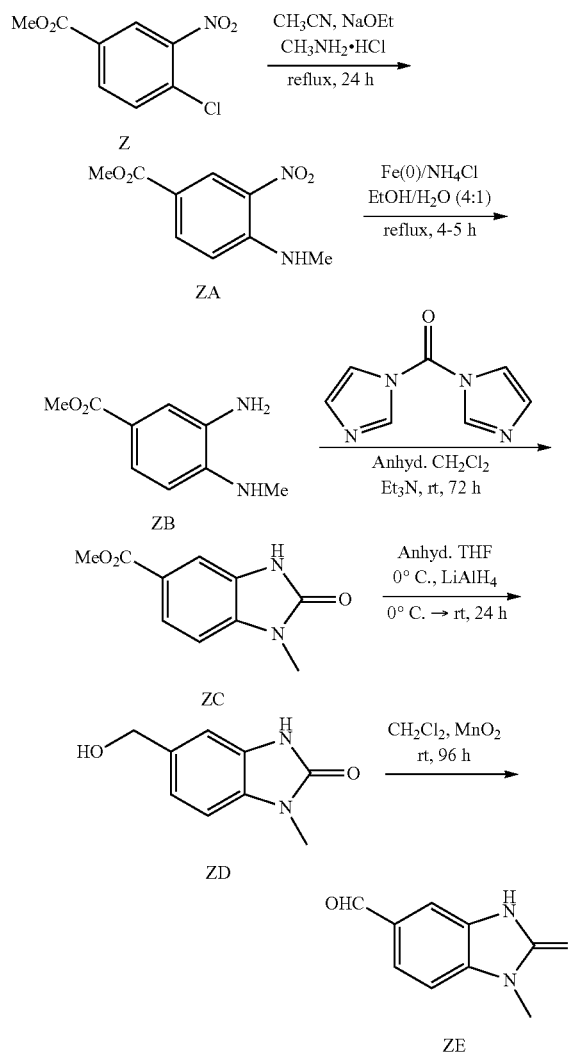

The chloro compound Z (5.0 g, 23.2 mmol) was dissolved in anhydrous CH$_3$CN (25 mL) and NaOEt (4.6 g, 56.08 mmol) followed by methylamine hydrochloride (3.14 g, 46.5 mmol) were added. The mixture was refluxed for 48 h, cooled to room temperature and quenched by dropwise addition of methanol (5 mL) at 0° C. The reaction was diluted with water and the organic layer was separated. The aqueous layer was washed with additional amount of ethyl acetate (3×30 mL). The organic layers were combined, dried over Na$_2$SO$_4$ and concentrated under vacuo on a rotary evaporator to obtain a yellow solid. The solid was dissolved in CH$_2$Cl$_2$ (20 mL) and 2 N HCl (in ether) was added. The solution was then stirred at room temperature for 2-4 h and the supernatant was drained off. The precipitated HCl salt was washed again with additional amount of CH$_2$Cl$_2$ (3×10 mL). The yellow HCl salt of compound ZA was dried in a vacuum oven at 40° C. for 4 h. The nitro compound ZA (2.03 g, 8.13 mmol) was dissolved in a 3:1 mixture of ethanol and water (97 mL). Fe (0) (4.57 g, 81.78 mmol) and NH$_4$Cl (438 mg, 8.48 mmol) were added to the solution. The mixture was then refluxed at 120° C. for 4-5 h and concentrated under vacuo on a rotary evaporator. The crude product was dissolved in CH$_2$Cl$_2$ and filtered through a whatman filter paper (grade 8) and concentrated under vacuo on a rotary evaporator to obtain the desired amine ZB.

Synthesis of 5-((((3R,4R,6S)-6-(bis(4-fluorophenyl)methyl)-4-hydroxytetrahydro-2H-pyran-3-yl)amino)methyl)-1-methyl-1H-benzo[d]imidazol-2(3H)-one

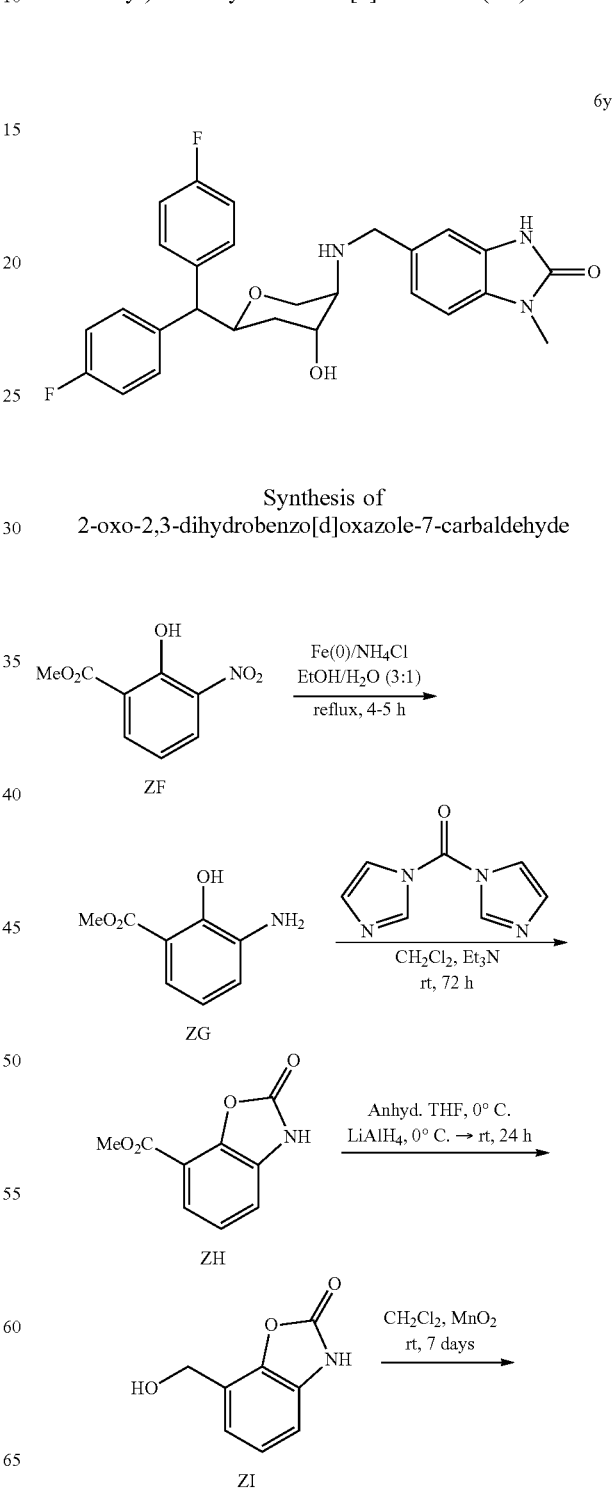

Synthesis of 2-oxo-2,3-dihydrobenzo[d]oxazole-7-carbaldehyde

The nitro compound ZF (1.37 g, 6.35 mmol) was dissolved in a 3:1 mixture of ethanol and water (83 mL). Fe(0) (3.88 g, 6.25 mmol) and NH$_4$Cl (0.37 g, 6.95 mmol) were added and the mixture was refluxed for 5 h. After cooling the reaction mixture to room temperature, it was filtered through a whatman filter paper (grade 8) to obtain the desired amine as brown solid (1.16 g, 100%) which was used in the next step without further purification. Compound ZG was dissolved in anhydrous CH$_2$Cl$_2$ (17 mL) and Et$_3$N (7.03 mL, 69.5 mmol) was added. Next, 1,1'-carbonyldiimidazole (2.03 g, 12.5 mmol) was added and the resulting mixture was stirred at room temperature for 72 h. The reaction was quenched by the addition of water (10 mL). The organic layer was separated and the aqueous layer was washed with additional amount of CH$_2$Cl$_2$ (3×10 mL). The organic layers were combined, dried over Na$_2$SO$_4$ and concentrated under vacuo on a rotary evaporator to obtain a yellowish white solid (1.34 g, 100%). Compound ZH was dissolved in anhydrous THF (16 mL) and cooled to 0° C. in an ice-bath. After the addition of LiAlH$_4$ (392 mg, 10.4 mmol), the reaction mixture was then stirred at room temperature for 24 h under a steady flow of N$_2$. The reaction was cooled to 0° C. and quenched by the addition of methanol, NH$_4$Cl and rochelle's salt. After dilution with additional ethyl acetate (16 mL), the organic layer was separated and the aqueous layer was with additional amount of ethyl acetate (3×10 mL). The organic layers were combined, dried over Na$_2$SO$_4$ and concentrated under vacuo on a rotary evaporator to obtain brownish solid (160 mg, 14%). Compound ZI (120 mg, 0.73 mmol) was dissolved in a 4:1 mixture of CH$_2$Cl$_2$ methanol (5 mL) and MnO$_2$ (250 mg, 2.91 mmol). The mixture was stirred for 7 days at room temperature, after which it was filtered through whatman filter paper (grade 8). The filtrate was concentrated under vacuo on a rotary evaporator to obtain a yellow solid. The crude product was purified via a preparative thin layer chromatography to obtain the desired aldehyde ZJ as light yellow solid (80 mg, 68%).

Synthesis of 7-((((3R,4R,6S)-6-(bis(4-fluorophenyl) methyl)-4-hydroxytetrahydro-2H-pyran-3-yl)amino) methyl)benzo[d]oxazol-2(3H)-one

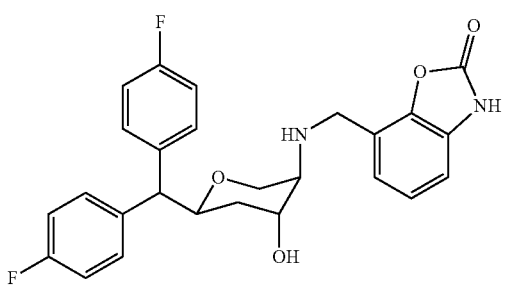

Synthesis of (2S,4R,5R)-2-benzhydryl-5-(((6-methoxypyridin-3-yl)methyl)amino)tetrahydro-2H-pyran-4-ol

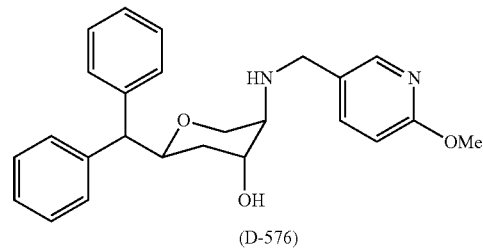

$^1$H NMR (500 MHz, CDCl$_3$): δ 8.04 (s, 1H), 7.55 (dd, J=2.1, 8.6 Hz, 1H), 7.06-7.40 (m, 11H), 6.69 (d, J=8.6 Hz, 1H), 4.42-4.55 (m, 1H), 3.85-4.00 (m, 4H), 3.74-3.84 (m, 2H), 3.66 (d, J=13.1 Hz, 1H), 2.42 (br s, 1H), 1.65-1.76 (m, 1H), 1.37-1.47 (m, 1H). $^{13}$C NMR (125 MHz, CDCl$_3$): δ 163.5, 146.1, 142.0, 141.9, 139.0, 128.6, 128.4, 128.3, 126.5, 126.3, 110.7, 73.5, 67.4, 64.7, 56.7, 56.2, 53.4, 48.1, 33.4. [α]$^{25}_D$=(−)44.7°, c=1 in MeOH. The product was converted into the corresponding hydrochloride salt; mp: 190-195° C. Anal. Calcd for [C$_{25}$H$_{28}$N$_2$O$_3$.2HCl] C, H, N.

Synthesis of (2S,4R,5R)-2-benzhydryl-5-((3-fluoro-4-methoxybenzyl)amino)tetrahydro-2H-pyran-4-ol

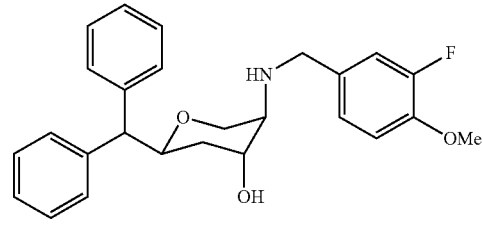

Amine 7 (60 mg, 0.21 mmol) was reacted with 3-fluoro-4-methoxybenzaldehyde (36 mg, 0.23 mmol), glacial acetic acid (16 μL, 0.27 mmol), and Na(OAc)$_3$BH (80 mg, 0.36 mmol) in a mixture of 1,2-dichloroethane (3 mL) and methanol (1 mL). The residue was purified by gradient silica gel column chromatography using a mixture of dichloromethane and methanol (100:1 to 6:1) to afford corresponding compound 8b (D-580) as colorless syrup (60 mg, 68%) as a colorless syrup. $^1$H NMR (500 MHz, CDCl$_3$): δ 7.12-7.39 (m, 10H), 7.07 (dd, J=12.2, 1.8 Hz, 1H), 6.97 (d, J=8.2 Hz, 1H), 6.87 (t, J=8.6 Hz, 1H), 4.49 (dt, J=10.4, 2.1 Hz, 1H), 3.87-3.98 (m, 3H), 3.86 (s, 3H0, 3.80 (d, J=13.4 Hz, 1H), 3.75 (d, J=11.9 Hz, 1H), 3.63 (d, J=13.1 Hz, 1H), 2.41 (s, 1H), 1.85 (br s, 1H), 1.66-1.76 (m, 1H), 1.37-1.47 (m, 1H). $^{13}$C NMR (125 MHz, CDCl$_3$): δ 153.4, 151.4, 146.6, 146.5, 142.1, 142.0, 133.5, 133.4, 128.6, 128.4, 128.3, 126.5, 126.3, 123.6, 123.5, 115.8, 115.7, 113.3, 73.6, 67.5, 64.8, 56.6, 56.4, 56.3, 50.4, 33.4. [α]$^{25}_D$=(−)53.9°, c=1 in CH$_2$Cl$_2$. The product was converted into the corresponding hydrochloride salt; mp: 190-195° C. Anal. Calcd for [C$_{26}$H$_{28}$FNO$_3$.HCl.H$_2$O] C, H, N.

Synthesis of (2S,4R,5R)-2-benzhydryl-5-((2-fluoro-4-methoxybenzyl)amino)tetrahydro-2H-pyran-4-ol

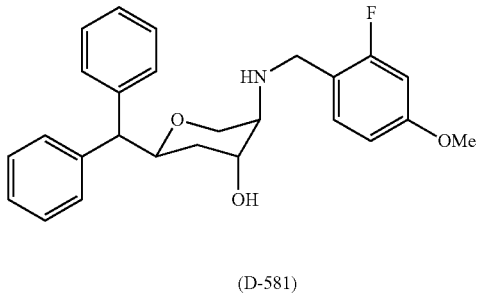

(D-581)

Amine 7 (60 mg, 0.21 mmol) was reacted with 2-fluoro-4-methoxybenzaldehyde (36 mg, 0.23 mmol), glacial acetic acid (16 μL, 0.27 mmol), and Na(OAc)$_3$BH (80 mg, 0.36 mmol) in a mixture of 1,2-dichloroethane (3 mL) and methanol (1 mL). The residue was purified by gradient silica gel column chromatography using a mixture of dichloromethane and methanol (100:1 to 6:1) to afford corresponding compound 8c (D-581) as colorless syrup (60 mg, 68%) as a white solid. $^1$H NMR (500 MHz, CDCl$_3$): δ 7.11-7.38 (m, 11H), 6.64 (dd, J=8.6, 2.1 Hz, 1H), 6.58 (dd, J=11.9, 2.4 Hz, 1H), 4.48 (dt, J=10.1, 2.4 Hz, 1H), 3.91-3.98 (m, 2H), 3.88 (dd, J=11.9, 2.1 Hz, 1H), 3.80 (d, J=13.4 Hz, 1H), 3.76 (s, 3H), 3.68-3.75 (m, 2H), 2.42 (m, 1H), 1.86 (s, 1H), 1.65-1.78 (m, 1H), 1.35-1.46 (m, 1H). $^{13}$C NMR (125 MHz, CDCl$_3$): δ 162.5, 160.6, 160.0, 159.9, 142.1, 142.0, 130.7, 130.6, 128.6, 128.4, 128.3, 128.3, 126.5, 126.3, 119.0, 118.9, 109.8, 109.7, 101.6, 101.4, 73.6, 67.3, 65.0, 56.7, 56.4, 55.5, 44.4, 33.4. [α]$^{25}_D$=(−)54.1°, c=1 in CH$_2$Cl$_2$. The product was converted into the corresponding hydrochloride salt; mp: 170-175° C. Anal. Calcd for [C$_{26}$H$_{28}$FNO$_3$.HCl.H$_2$O] C, H, N.

Synthesis of tert-butyl 3-((((3R,4R,6S)-6-benzhydryl-4-hydroxytetrahydro-2H-pyran-3-yl)amino)methyl)-5-methoxy-1H-indole-1-carboxylate

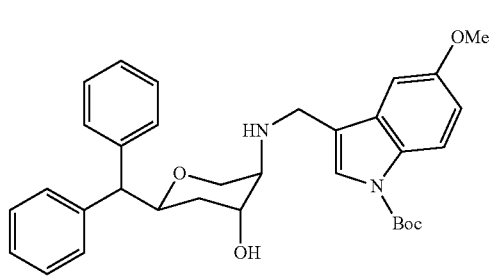

Amine 7 (60 mg, 0.21 mmol) was reacted with tert-butyl 3-formyl-5-methoxy-1H-indole-1-carboxylate (70 mg, 0.25 mmol), glacial acetic acid (16 μL, 0.22 mmol), and Na(OAc)$_3$BH (81 mg, 0.38 mmol) in a mixture of 1,2-dichloroethane (3 mL) and methanol (1 mL). The residue was purified by gradient silica gel column chromatography using a mixture of dichloromethane and methanol (100:1 to 6:1) to afford corresponding compound 8d as light yellow syrup (40 mg, 44%) $^1$H NMR (600 MHz, CDCl$_3$): δ 8.0 (br s, 1H), 7.46 (br s, 1H), 7.34 (d, J=7.4 Hz, 2H), 7.15-7.32 (m, 10H), 7.07 (d, J=2.5 Hz, 1H), 6.20 (dd, J=8.9, 2.5 Hz, 1H), 4.5 (dt, J=10.2, 2.3 Hz, 1H), 3.89-4.07 (m, 4H), 3.77-3.88 (m, 5H), 2.51 (d, J=2.5 Hz, 1H), 2.02 (br s, 2H), 1.67-1.78 (m, 1H), 1.64 (s, 9H), 1.38-1.46 (m, 1H).

Synthesis of (2S,4R,5R)-2-benzhydryl-5-(((5-methoxy-1H-indol-3-yl)methyl)amino)tetrahydro-2H-pyran-4-ol

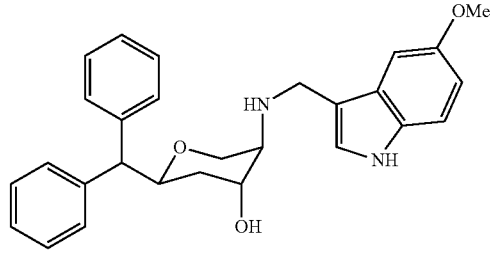

(D-598)

Compound 8d (170 mg, 0.31 mmol) was dissolved in anhydrous CH$_2$Cl$_2$ (5 mL) and TFA (5 mL) was added to the solution slowly at room temperature. The resulting mixture was stirred at room temperature for 2 h. Then it was quenched by the addition of saturated NaHCO$_3$ at 0° C. The organic layer was separated and the aqueous layer was extracted with additional CH$_2$Cl$_2$ (3×5 mL). The organic layers were combined, dried over Na$_2$SO$_4$ and concentrated under vacuo on a rotary evaporator. The crude product was purified via gradient silica gel column chromatography using a mixture of CH$_2$Cl$_2$ and MeOH (100:1 to 6:1) to obtain the desired product as yellowish white syrup (80 mg, 58%). $^1$H NMR (600 MHz, CDCl$_3$): δ 8.00 (br s, 1H), 7.3 (d, J=7.4 Hz, 2H), 7.12-7.31 (m, 10H), 7.09 (d, J=2.0 Hz, 1H), 6.86 (dd, J=8.7, 2.3 Hz, 1H), 4.53 (dt, J=9.9, 2.5 Hz, 1H), 4.15 (d, J=13.7 Hz, 1H), 4.09 (br s, 1H), 3.93-4.03 (m, 3H), 3.90 (d, J=11.9 Hz, 1H), 3.80 (s, 3H), 2.67 (s, 1H), 1.67-1.75 (m, 1H), 1.41-1.50 (m, 1H). $^{13}$C NMR (150 MHz, CDCl$_3$): δ 154.2, 142.0, 141.9, 128.7, 128.4, 128.3, 127.2, 126.6, 126.3, 125.0, 124.5, 112.5, 112.1, 100.4, 73.9, 63.6, 56.4, 56.2, 55.8, 33.3, 32.2, 29.7, 23.4. [α]$^{25}_D$=(−)71.0°, c=1 in MeOH. The product was converted into the corresponding hydrochloride salt; mp: 160-165° C. Anal. Calcd for [C$_{28}$H$_{30}$N$_2$O$_3$.HCl.H$_2$O] C, H, N.

Synthesis of 3-methylbenzo[d]oxazole-2(3H)-thione

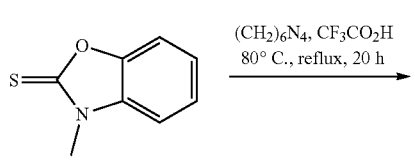

3-methylbenzo[d]oxazole-2(3H)-thione (1.0 g, 6.06 mmol, ZK) was taken in an oven dried RB flask equipped with magnetic stir bar. To the flask, hexamethylenetetramine (2.35 g, 18.17 mmol) was added, followed by TFA (10 mL). The resulting mixture was refluxed at 80° C. for about 24 h. The reaction mixture was then cooled and poured into ice-water. The solution was then basified with saturated NaHCO$_3$ and extracted with ethyl acetate. The aqueous layer was extracted further with ethyl acetate. The organic layers were combined, dried over Na$_2$SO$_4$ and concentrated under reduced pressure on a rotary evaporator to obtain the desired aldehyde ZL as yellow solid (70%).

Synthesis of 6-((((3R,4R,6S)-6-benzhydryl-4-hydroxytetrahydro-2H-pyran-3-yl)amino)methyl)-3-methylbenzo[d]oxazole-2(3H)-thione

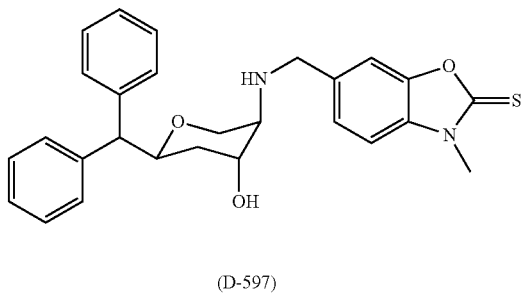

(D-597)

Amine 7 (100 mg, 0.35 mmol) was reacted with 3-methyl-2-thioxo-2,3-dihydrobenzo[d]oxazole-6-carbaldehyde (82 mg, 0.42 mmol), glacial acetic acid (32 μL, 0.44 mmol), and Na(OAc)$_3$BH (140 mg, 0.64 mmol) in a mixture of 1,2-dichloroethane (6 mL) and methanol (2 mL). The residue was purified by gradient silica gel column chromatography using a mixture of dichloromethane and methanol (100:1 to 6:1) to afford corresponding compound 8f (D-597) as light yellow solid syrup (45 mg, 50%). $^1$H NMR (600 MHz, CDCl$_3$): δ 7.40 (s, 1H), 7.34 (d, J=7.6 Hz, 2H), 7.12-7.31 (m, 10H), 6.92 (d, J=8.0 Hz, 1H), 4.50 (dt, J=10.2, 2.1 Hz, 1H), 3.89-4.0 (m, 3H), 3.88 (d, J=13.7 Hz, 1H), 3.77 (d, J=11.4 Hz, 1H), 3.72 (d, J=13.2 Hz, 1H), 3.40 (s, 3H), 2.44 (s, 1H), 2.0 (br s, 1H), 1.65-1.75 (m, 1H), 1.39-1.48 (m, 1H). $^{13}$C NMR (150 MHz, CDCl$_3$): δ 170.1, 142.0, 141.9, 136.7, 135.6128.6, 128.4, 128.3, 128.3, 126.5, 126.3, 126.3, 122.6, 122.1, 110.2, 73.5, 67.3, 64.7, 56.6, 56.3, 50.9, 33.4, 29.0. $[\alpha]^{25}_D$=(−)79.0°, c=1 in CH$_2$Cl$_2$. The product was converted into the corresponding hydrochloride salt; mp: 185-190° C. Anal. Calcd for [C$_{27}$H$_{28}$N$_2$O$_3$S.HCl.H$_2$O] C, H, N.

Synthesis of Equatorial Isomer of D-473

1. (2S,4S,5R)-5-azido-2-(bis(4-fluorophenyl)methyl)tetrahydro-2H-pyran-4-ol

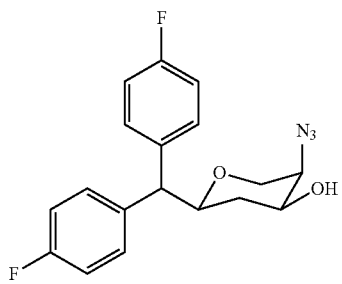

The azido compound 9 (196 mg, 0.57 mmol) was dissolved in anhydrous CH$_2$Cl$_2$ (4 mL) under a steady flow of N$_2$ and cooled to −10° C. Then anhydrous pyridine (0.28 mL, 3.43 mmol) was added dropwise. After stirring the solution for 5 minutes, Tf$_2$O was added very slowly and the resulting mixture was stirred at the same temperature until the reaction was complete (~3-4 h). Water (0.22 mL, 12.22 mmol) was added to the reaction mixture and the resulting solution was refluxed at 90° C. for 2 h. TLC showed that the reaction was incomplete after 2 h. Additional amount of water (1 mL) was added and the reaction mixture was refluxed for additional 70 h. Next, the organic layer was separated and the aqueous layer was extracted with additional CH$_2$Cl$_2$ (3×5 mL). The organic layers were combined, dried over Na$_2$SO$_4$ and concentrated under vacuo on a rotary evaporator. The crude product was purified by gradient silica gel column chromatography using a mixture of hexanes and ethyl acetate (10:1 to 1:1) to obtain the desired product 11 as a white solid (100 mg, 51%). $^1$H NMR (400 MHz, CDCl$_3$): δ 7.24-7.33 (m, 2H), 7.11-7.20 (m, 2H), 6.90-7.02 (m, 4H), 4.38 (dt, J=10.2, 2.0 Hz, 1H), 4.01 (dd, J=12.5, 1.9 Hz, 1H), 3.94-4.01 (m, 1H), 3.84-3.94 (m, 2H), 3.28 (d, J=1.7 Hz, 1H), 1.96 (br s, 1H), 1.70-1.82 (m, 1H), 1.38-1.49 (m, 1H). $^{13}$C NMR (100 MHz, CDCl$_3$): δ 162.8, 162.7, 160.3, 160.2, 137.4, 137.3, 137.2, 137.1, 129.9, 129.8, 129.7, 129.7, 115.6, 115.4, 115.3, 115.1, 73.3, 65.9, 64.6, 59.1, 55.0, 33.1. $[\alpha]^{25}_D$=(−) 116.2°, c=1 in CH$_2$Cl$_2$.

2. (2S,4S,5R)-5-amino-2-(bis(4-fluorophenyl)methyl)tetrahydro-2H-pyran-4-ol

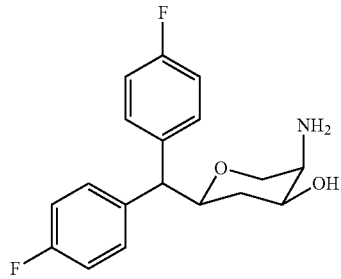

The azide 11 (100 mg, 0.29 mmol) was dissolved in MeOH and Pd/C was added (40 mg). The resulting mixture was stirred under a steady flow of H$_2$ (1 atm) for overnight. The solution was then filtered through whatman filter paper (grade 8) and the filtrate was concentrated under vacuo on a rotary evaporator to obtain the desired amine 12 as a colorless syrup (90 mg, 98%). $^1$H NMR (500 MHz, CDCl$_3$): δ 7.26 (dd, J=7.9, 5.5 Hz, 2H), 7.15 (dd, J=8.9, 5.5 Hz, 2H), 6.87-7.03 (m, 4H), 4.37 (dt, J=10.2, 2.1 Hz, 1H), 3.98 (dd, J=11.9, 1.8 Hz, 1H), 3.89 (d, J=8.9 Hz, 1H), 3.82 (d, J=3.1 Hz, 1H), 3.60 (d, J=11.6 Hz, 1H), 2.65 (s, 1H), 2.20 (br s, 3H), 1.61-1.79 (m, 1H), 1.33-1.48 (m, 1H). $^{13}$C NMR (125 MHz, CDCl$_3$): δ 162.5, 162.4, 160.5, 160.4, 137.7, 137.3, 129.9, 129.8, 129.7, 129.6, 115.5, 115.4, 115.3, 115.1, 73.7, 68.7, 68.1, 55.0, 51.0, 32.6. $[\alpha]^{25}_D$=(−) 64.0°, c=1 in CH$_2$Cl$_2$.

3. (2S,4S,5R)-2-(bis(4-fluorophenyl)methyl)-5-((4-methoxybenzyl)amino)tetrahydro-2H-pyran-4-ol

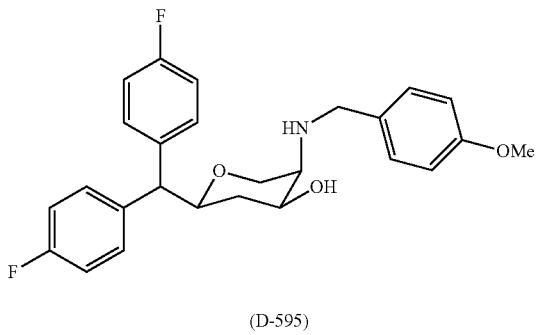

(D-595)

Amine 12 (60 mg, 0.19 mmol) was reacted with 4-methoxybenzaldehyde (32 mg, 0.23 mmol), glacial acetic acid (16 μL, 0.22 mmol), and Na(OAc)$_3$BH (73 mg, 0.34 mmol) in a mixture of 1,2-dichloroethane (3 mL) and methanol (1 mL). The residue was purified by gradient silica gel column chromatography using a mixture of dichloromethane and methanol (100:1 to 6:1) to afford corresponding compound 13 (D-595) as a light yellow solid (45 mg, 55%). $^1$H NMR (400 MHz, CDCl$_3$): δ 7.26 (dd, J=9.1, 5.4 Hz, 2H), 7.21 (d, J=8.6 Hz, 2H), 7.14 (dd, J=8.6, 5.4 Hz, 2H), 6.89-7.01 (m, 4H), 6.85 (d, J=9.0 Hz, 2H), 4.39 (dt, J=10.2, 2.4 Hz, 1H), 3.97-4.04 (m, 1H), 3.86-3.94 (m, 2H), 3.72-3.86 (m, 5H), 3.66 (d, J=13.0 Hz, 1H), 2.78 (br s, 2H), 2.48 (d, J=2.7 Hz, 1H), 1.61-1.75 (m, 1H), 1.34-1.46 (m, 1H). $^{13}$C NMR (100 MHz, CDCl$_3$): δ 162.7, 162.6, 160.3, 160.2, 158.8, 137.7, 137.4, 131.1, 129.9, 129.8, 129.7, 129.6, 129.4, 115.6, 115.4, 115.3, 115.1, 113.9, 73.6, 66.8, 64.4, 56.2, 55.2, 54.8, 50.4, 33.1. $[\alpha]^{25}_D$=(-)76.0°, c=1 in CH$_2$Cl$_2$. The product was converted into the corresponding hydrochloride salt; mp: 195-200° C. Anal. Calcd for [C$_{26}$H$_{27}$F$_2$N$_2$O$_3$·HCl·H$_2$O] C, H, N.

TABLE 1

Affinity of drugs at DAT, SERT, and NET in rat brain.

| Compound | DAT uptake, K$_i$, nM [$^3$H]DA$^a$ | SERT uptake, K$_i$, nM [$^3$H]-5-HT$^a$ | NET uptake, K$_i$, nM [$^3$H]DA$^a$ |
|---|---|---|---|
| 4c, D-501 | 167 ± 36 | 223 (5) ± 34 | 33.7 ± 7.9 |
| 4d, D-502 | 58.6 ± 11.8 | 281 ± 37 | 30.2 (7) ± 7.6 |
| 4e, D-503 | 209 ± 25 | 385 ± 42 | 44.2 (6) ± 9.4 |
| 4g, D-523 | 376 ± 68 | 27.2 ± 3.0 | 5.85 ± 1.27 |
| 2b, D-543 | 56.3 ± 1.1 | 13.6 ± 1.6 | 20.8 ± 4.6 |
| 4b, D-544 | 64.0 ± 6.1 | 9.60 ± 2.57 | 10.0 ± 3.5 |
| 4f, D-542 | 259 ± 44 | 3,017 ± 341 | 152 ± 29 |
| 4a, D-485 | 234 ± 11 | 2.68 ± 0.094 | 33.6 ± 18.7 |
| 2a, D-484 | 81.9 ± 17.9 | 0.71 ± 0.085 | 25.2 ± 5.3 |
| 6c, D-507 | 17 ± 1.7 | 54.0 ± 7.8 | 25.8 ± 5 |
| 6d, D-508 | 29.3 ± 2.4 | 68.4 ± 11.4 | 26.5 ± 6.6 |
| 6a, D-473 | 13.3 ± 2.0 | 46.7 ± 17.0 | 13.2 ± 3.5 |
| 6b, D-506 | 37.0 ± 7.5 | 400 (6) ± 80 | 10.2 (4) ± 0.6 |
| 6e, D-524 | 56.8 ± 7.6 | 129 ± 25 | 28.8 (5) ± 4.3 |
| 6f, D-525 | 25.3 ± 6.2 | 26.9 ± 2.6 | 25.8 ± 7.7 |
| 6g, D-526 | 25.6 ± 5.8 | 577 ± 94 | 4.91 (5) ± 0.63 |
| 6h, D-527 | 8.94 ± 2.20 | 107 ± 11 | 4.76 (4) ± 1.72 |
| 6i, D-528 | 7.94 ± 0.66 | 367 ± 52 | 14.6 (6) ± 2.9 |
| 6k, D-529 | 24.5 ± 1.2 | 339 ± 39 | 3.92 (5) ± 0.71 |
| 6m, D-530 | 15.3 (4) ± 3.3 | 320 ± 40 | 25.9 (5) ± 6.7 |
| 6n, D-531 | 13.1 (4) ± 5.0 | 334 ± 54 | 7.37 (6) ± 2.11 |
| 6o, D-536 | 41.3 ± 9.7 | 144 ± 26 | 56.6 ± 5.2 |
| 6p, D-537 | 20.1 ± 5.3 | 258 ± 26 | 28.4 ± 4.0 |

In Vivo Efficacy of D-525, Including Dosing and Schedule

Compound D-525 was evaluated in Force Swim test which is a well-known animal model of depression. The test procedure consisted of a pretest and test session separated by 24 h. Drugs or vehicle were administered orally (p.o) by following the timeline as described in the standard protocol. Each rat underwent a 5-min swim session following drug administration, which was videotaped and scored later.

All drugs were prepared freshly on the test days. Compound D-525 and imipramine were dissolved in deionized water. All drugs and vehicles were administered p.o. D-525 was administered at a dose of 12.5 and 25 mg/kg. An individual, blinded to the treatment, scored the videotapes for immobility. Immobility scores were analyzed by one way ANOVA test which indicated significant difference between drug treated animals and vehicle.

FIG. 11 provides a bar chart showing the effect of sub-chronic oral administration of vehicle and D-525 on the duration of immobility in the forced swimming test in rats. One way ANOVA analysis demonstrates significant effect among treatments: F (3.95)=8.12 (P<0.001). Dunnett's analysis showed that the effect of D-525 at two doses (12 and 25 mg/kg) immobility was statistically significant different compared to vehicle (P<0.01). Asterisks indicate a statistically significant difference toward control group that received saline p.o. **P<0.01. Each treatment group contained four to seven rats.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:
1. A compound having formula I:

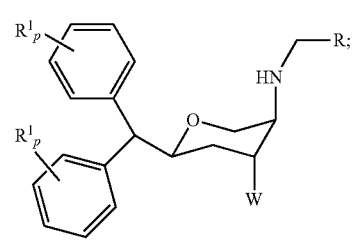

or a pharmaceutically acceptable salt thereof;
wherein;
p is 0 to 5;
R is

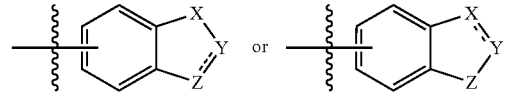

W is OH;
R$^1$ is C$_{1-4}$ alkyl, C$_{2-6}$ alkenyl, C$_{2-6}$ optionally halogenated alkynyl, C$_{2-6}$ hydroxyalkynyl, halo, —CN, —COOR$^2$, C$_{5-10}$ cycloalkyl, C$_{2-18}$ alkenyl, —OH, —NO$_2$, —NHR$^2$, or —OR$^2$; and
R$^2$ is C$_{1-8}$ alkyl, C$_{5-6}$ cycloalkyl, or C$_{2-8}$ alkenyl;
the dashed line is an optional bond;
X and Z are each independently S, N, O, or NR$^4$;

Y is C=O, C=S, N, or NR⁴; and
R⁴ is H or $C_{1-8}$ alkyl.
2. A compound having a formula selected from the group consisting of:
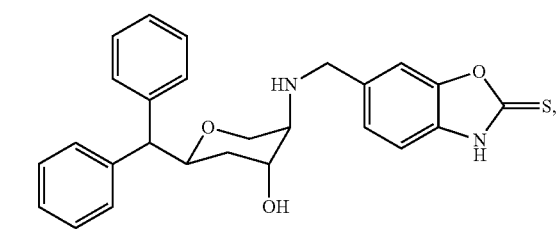
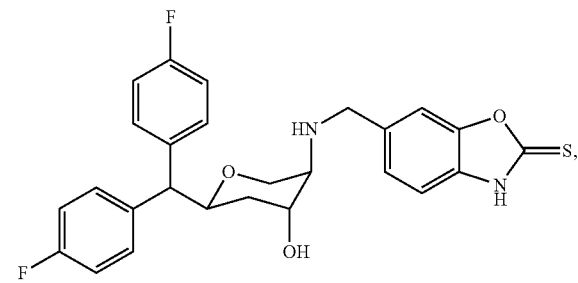
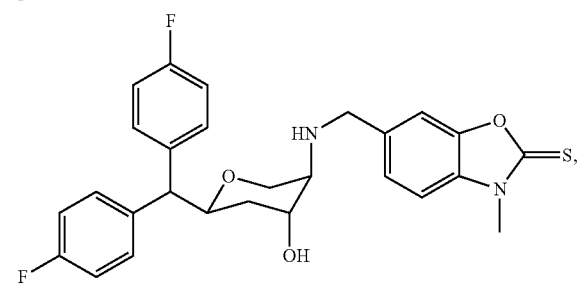
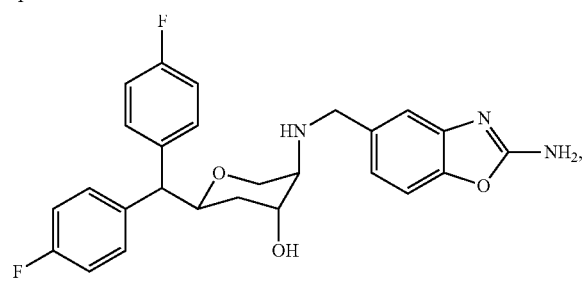
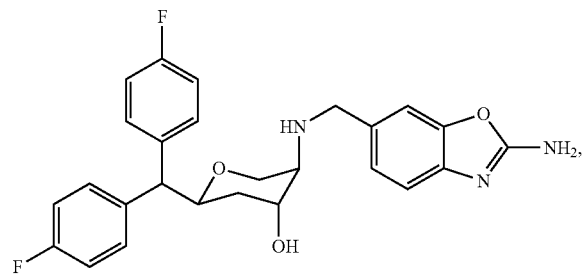
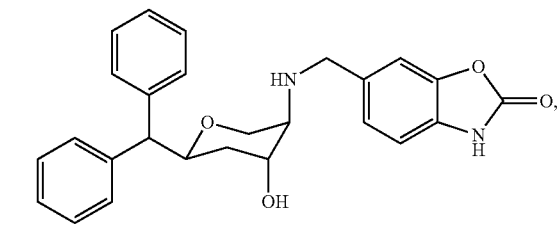
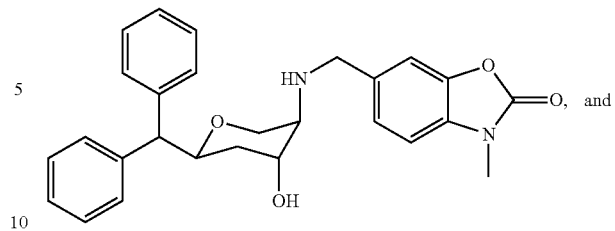
pharmaceutically acceptable salts thereof.
3. The compound of claim 1 having a formula selected from the group consisting of:
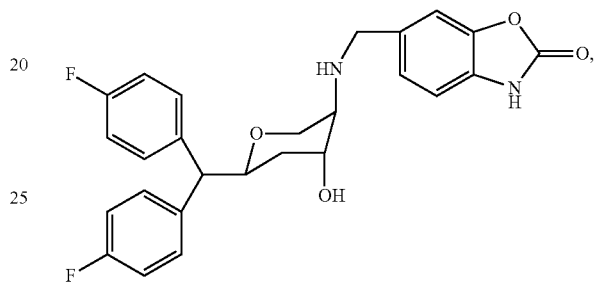
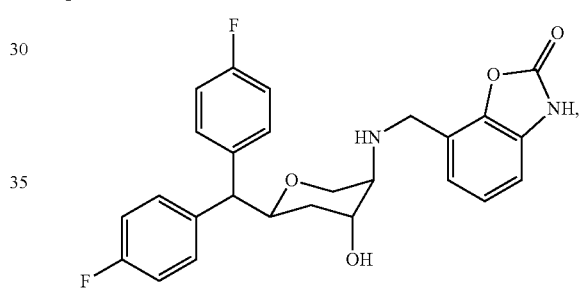
and pharmaceutically acceptable salts thereof.
4. A compound selected from the group consisting of:
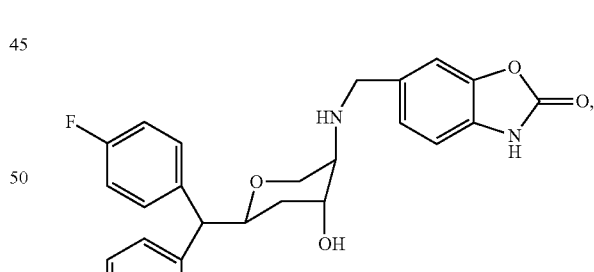
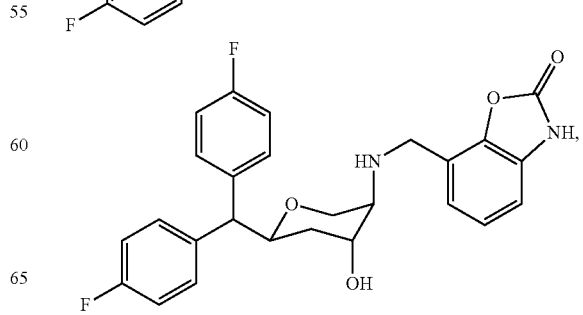

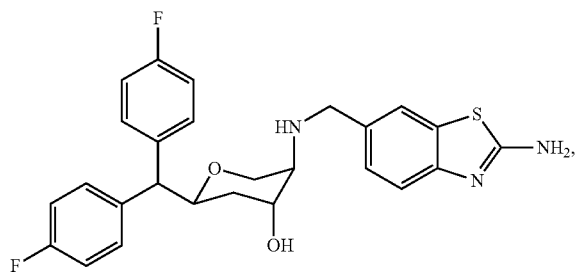
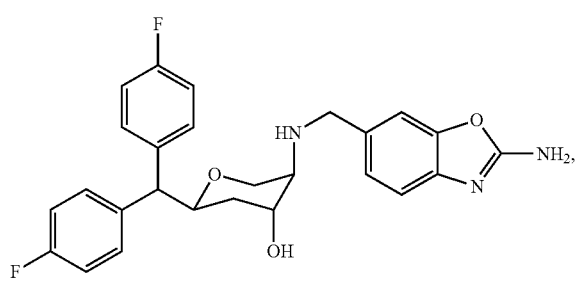
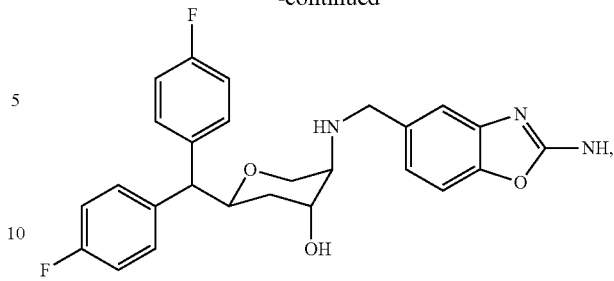
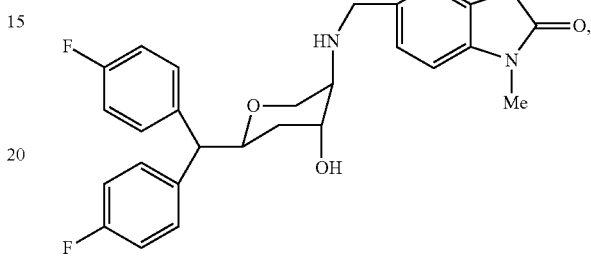
D-525
and pharmaceutically acceptable salts thereof.
* * * * *